(12) United States Patent
Bailly et al.

(10) Patent No.: US 12,059,336 B2
(45) Date of Patent: Aug. 13, 2024

(54) KITS FOR SURGICAL REPAIR OF SOFT TISSUE DEFECTS AND COMPONENTS, PACKAGING, AND METHODS OF USE THEREOF

(71) Applicant: SOFRADIM PRODUCTION, Trevoux (FR)

(72) Inventors: Pierre Bailly, Caluire-et-Cuire (FR); Genevieve Doucet, Villefranche sur Saone (FR); Thierry Brune, Jarnioux (FR)

(73) Assignee: SOFRADIM PRODUCTION, Trevoux (FR)

( * ) Notice: Subject to any disclaimer, the term of this patent is extended or adjusted under 35 U.S.C. 154(b) by 434 days.

(21) Appl. No.: 17/202,127

(22) Filed: Mar. 15, 2021

(65) Prior Publication Data

US 2021/0330437 A1    Oct. 28, 2021

(30) Foreign Application Priority Data

Apr. 23, 2020    (EP) .................................... 20315213

(51) Int. Cl.
*A61F 2/00*    (2006.01)
(52) U.S. Cl.
CPC .... *A61F 2/0063* (2013.01); *A61F 2002/0072* (2013.01); *A61F 2220/0075* (2013.01)
(58) Field of Classification Search
CPC ............ A61F 2/0063; A61F 2002/0072; A61F 2220/0075; A61F 2/0095
See application file for complete search history.

(56) References Cited

U.S. PATENT DOCUMENTS

| | | | |
|---|---|---|---|
| 5,397,332 A | 3/1995 | Kammerer et al. | |
| 5,464,403 A | 11/1995 | Kieturakis et al. | |
| 8,920,483 B2* | 12/2014 | Swanick | A61F 2/0063 606/151 |
| 2004/0039453 A1* | 2/2004 | Anderson | A61B 17/06109 623/23.72 |
| 2007/0112361 A1* | 5/2007 | Schonholz | A61B 17/00234 606/151 |

(Continued)

FOREIGN PATENT DOCUMENTS

| | | |
|---|---|---|
| EP | 0625334 A1 | 11/1994 |
| WO | 2003096929 | 6/2004 |

(Continued)

OTHER PUBLICATIONS

Extended European Search Report issued in European Application No. 20315213.7 dated Oct. 22, 2020.

(Continued)

*Primary Examiner* — Christine H Matthews
*Assistant Examiner* — Marc D. Honrath
(74) *Attorney, Agent, or Firm* — Weber Rosselli & Cannon LLP

(57) ABSTRACT

The present disclosure describes kits for surgical repair of soft tissue defects, including hernias. The kits include any combination of components selected from an implantable sheet, a central tie, a delivery tool, a rolling device, and an insertion member. Packaging for the kits and/or components and methods of using the kits and/or components are also provided.

17 Claims, 29 Drawing Sheets

(56) References Cited

U.S. PATENT DOCUMENTS

| | | | |
|---|---|---|---|
| 2011/0295283 A1* | 12/2011 | Darois | A61F 2/0063 |
| | | | 606/151 |
| 2012/0232334 A1* | 9/2012 | Bell | A61B 17/3423 |
| | | | 606/213 |
| 2013/0310637 A1 | 11/2013 | Iceman et al. | |
| 2018/0028303 A1* | 2/2018 | Guo | A61B 17/06004 |
| 2019/0110878 A1* | 4/2019 | Rathbun | A61B 17/06166 |

FOREIGN PATENT DOCUMENTS

| | | |
|---|---|---|
| WO | 2007056297 A2 | 5/2007 |
| WO | 2010059234 A1 | 5/2010 |
| WO | 2013020107 A1 | 2/2013 |

OTHER PUBLICATIONS

Extended European Search Report issued in European Patent Application No. 21170306.1 dated Aug. 16, 2021.

* cited by examiner

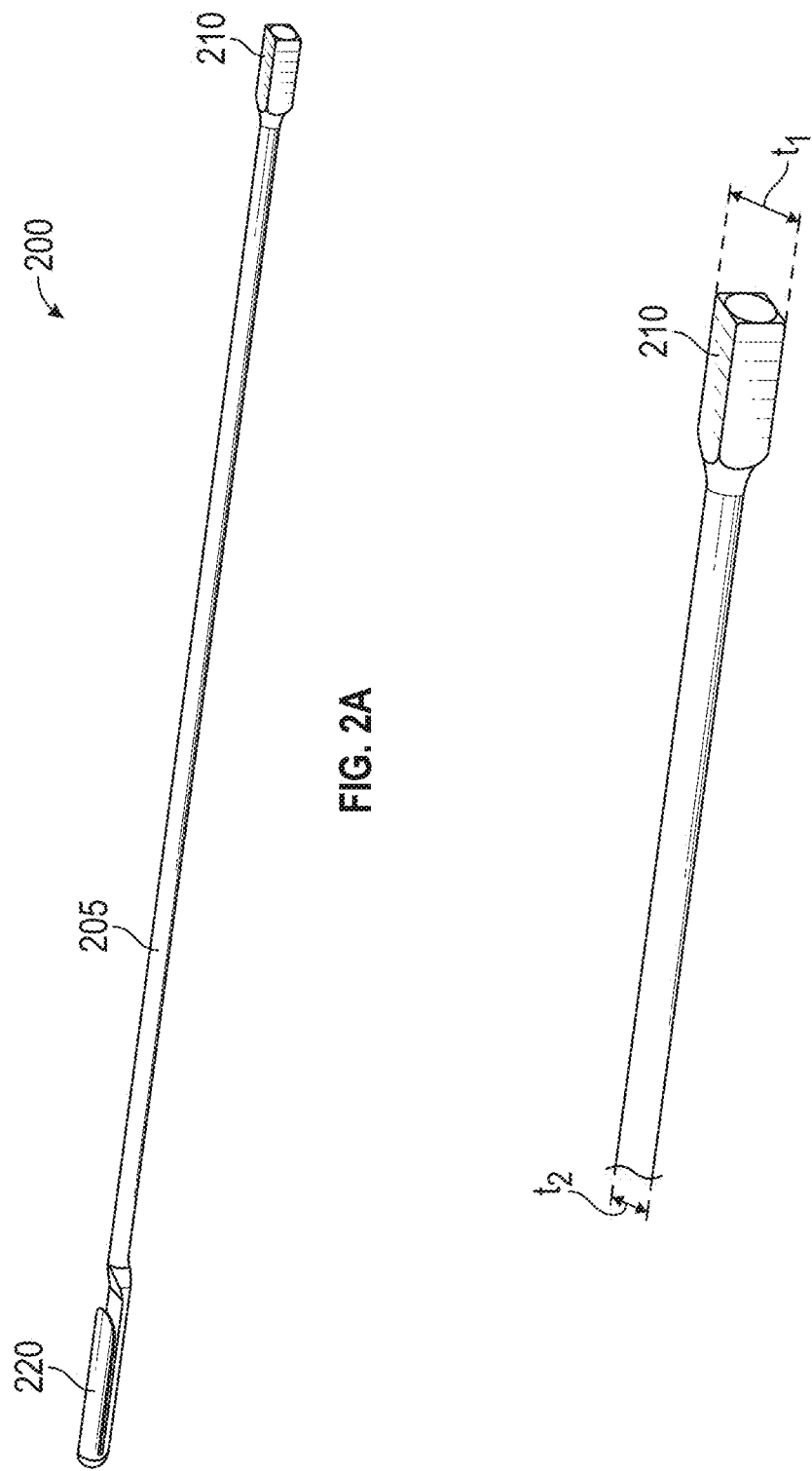

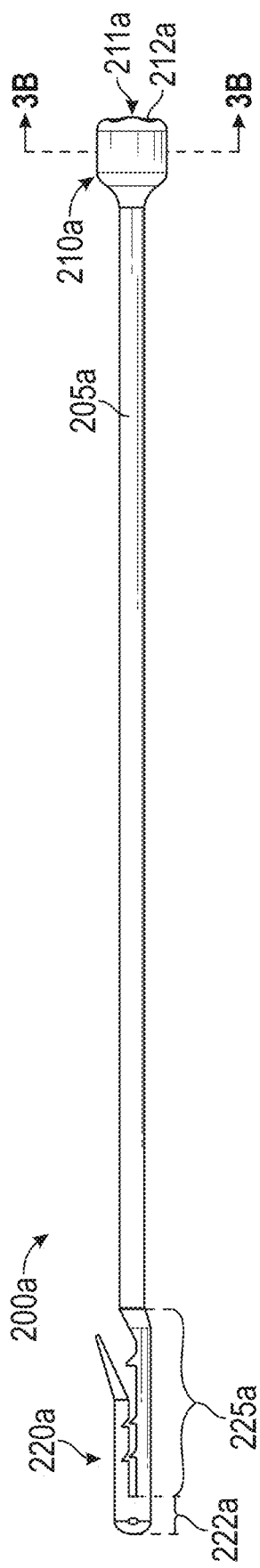
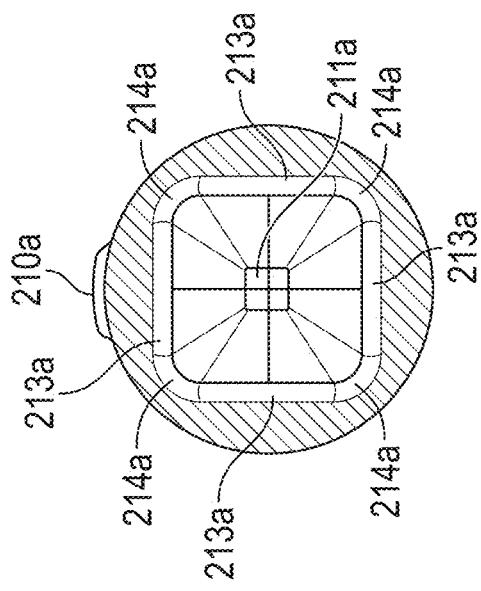
FIG. 3A
FIG. 3B

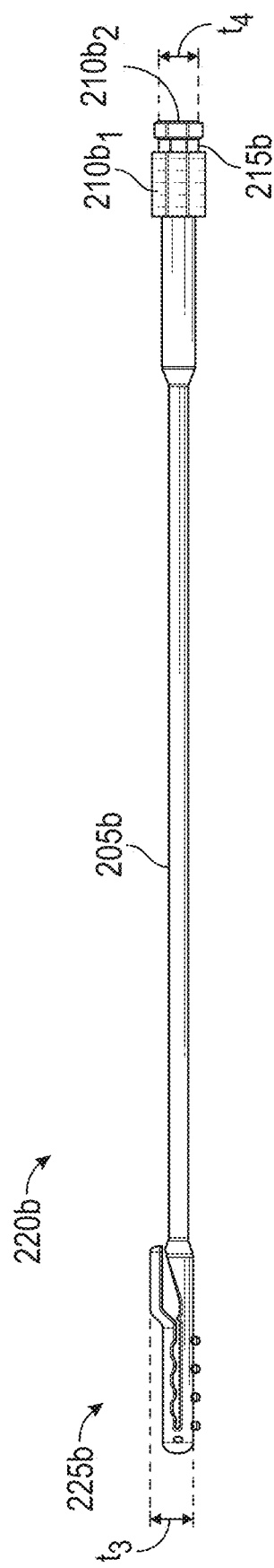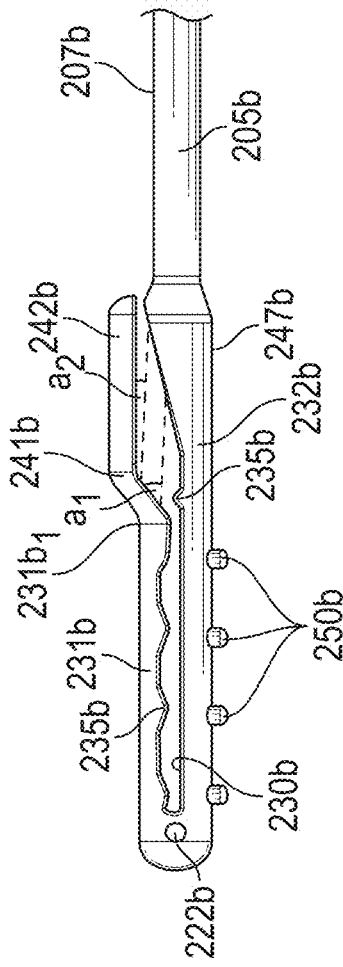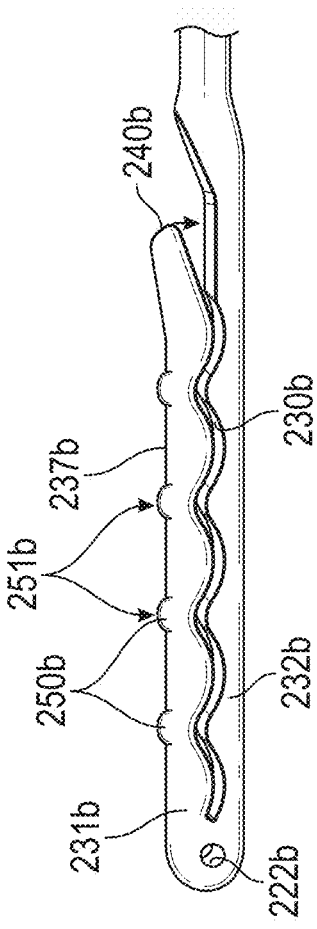
FIG. 4A
FIG. 4B
FIG. 4C

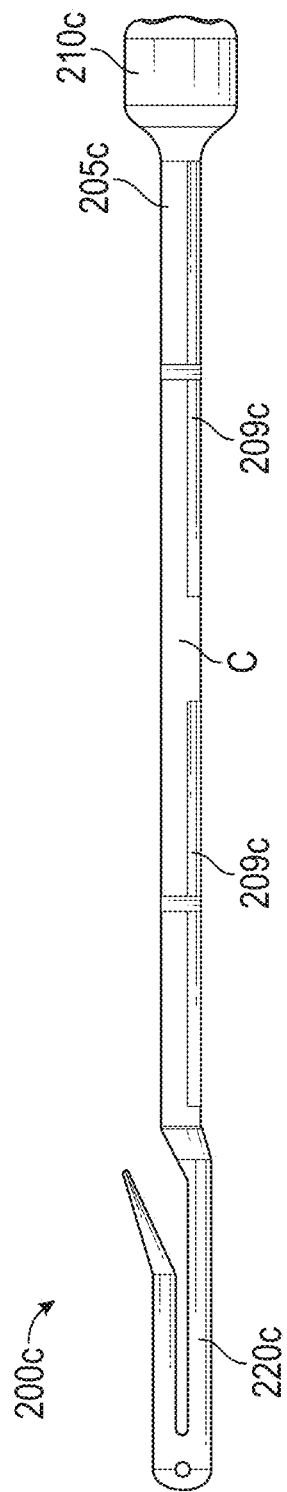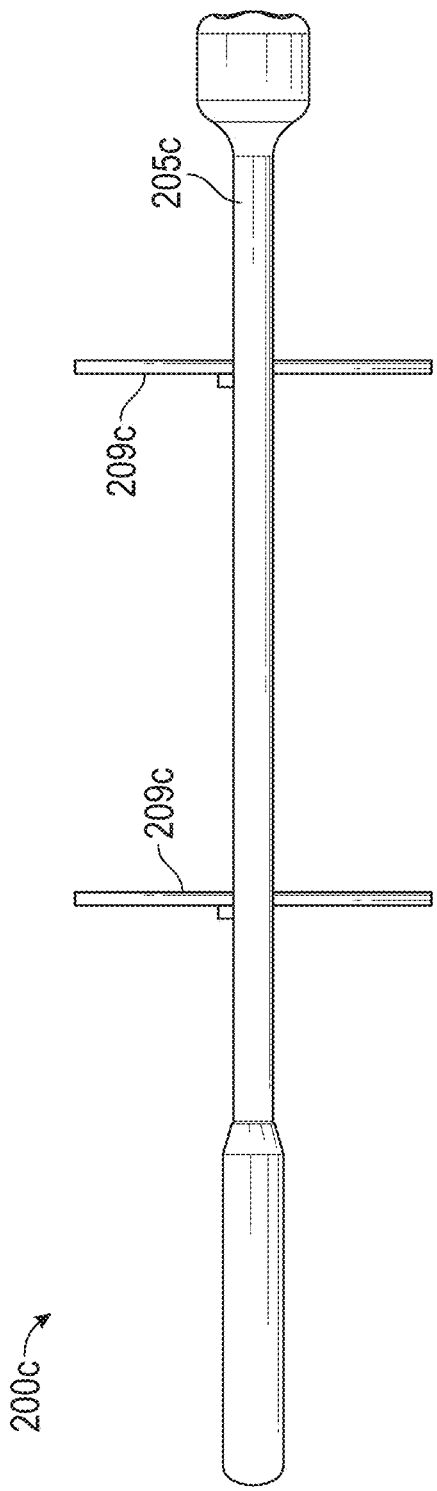
FIG. 5A
FIG. 5B

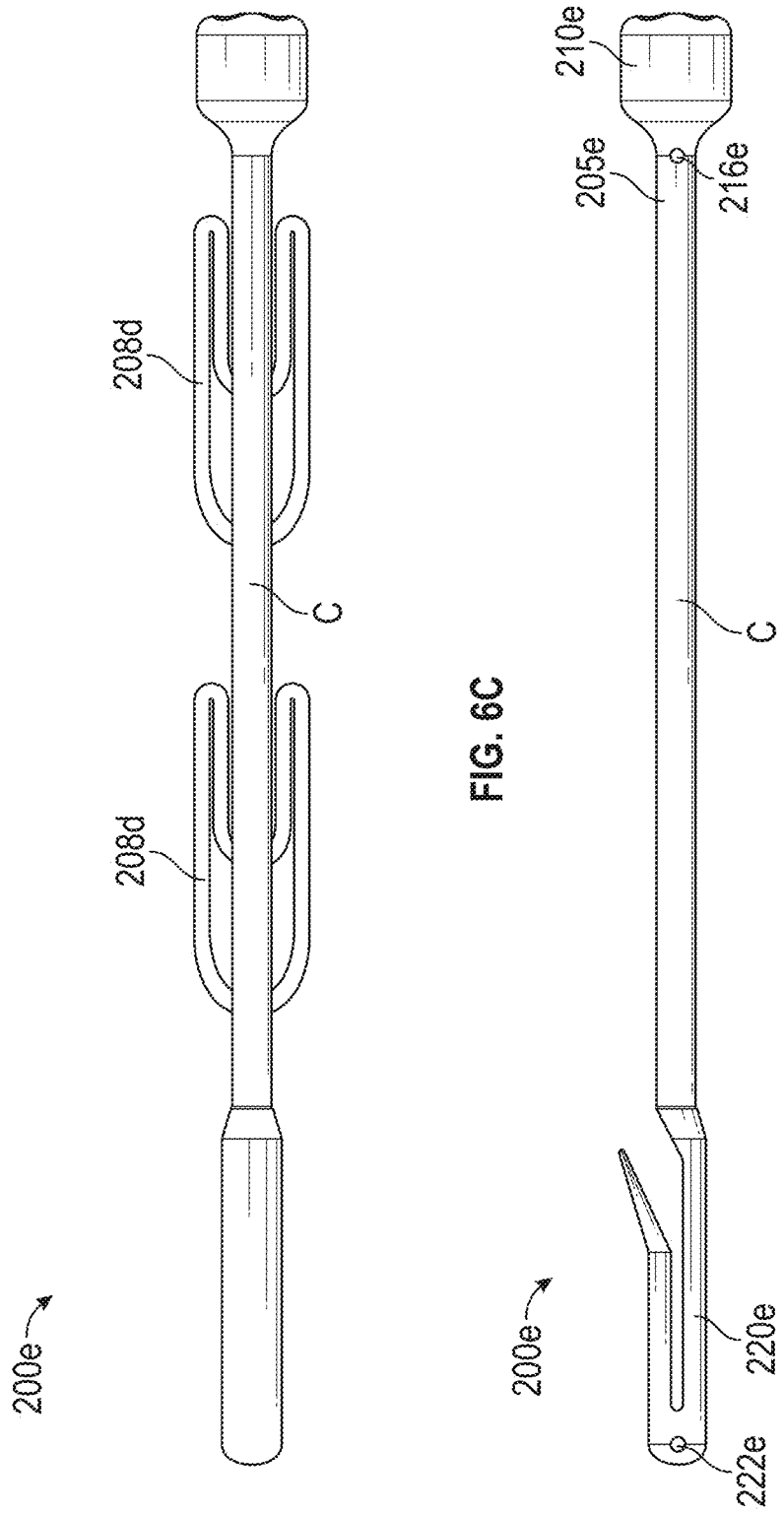

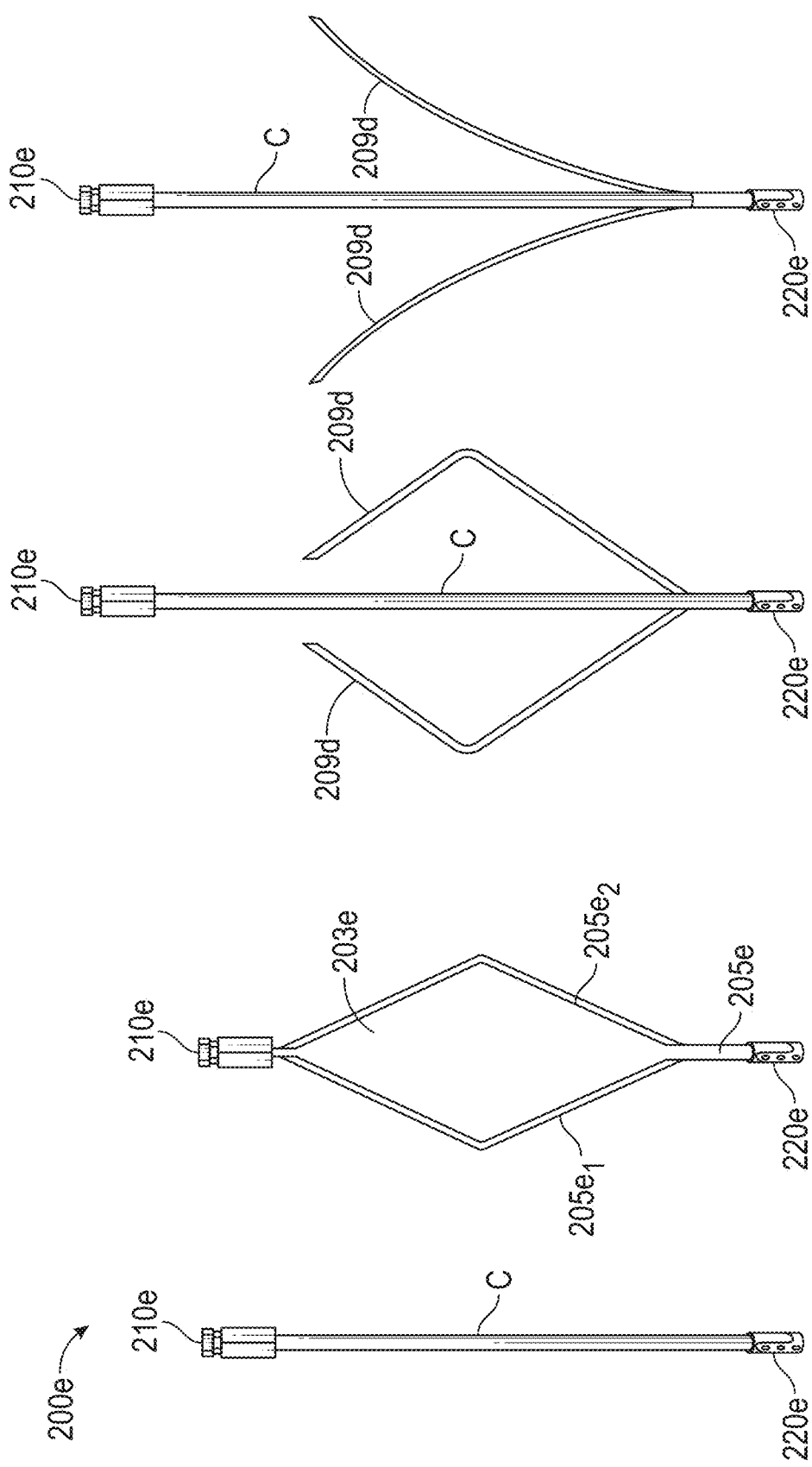

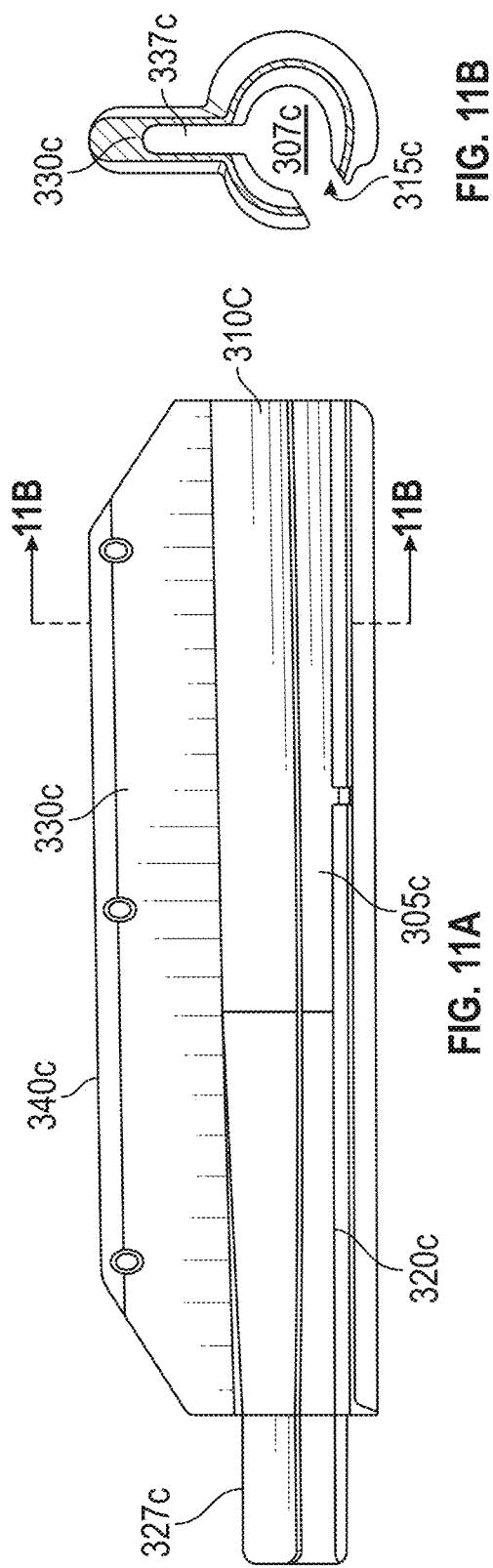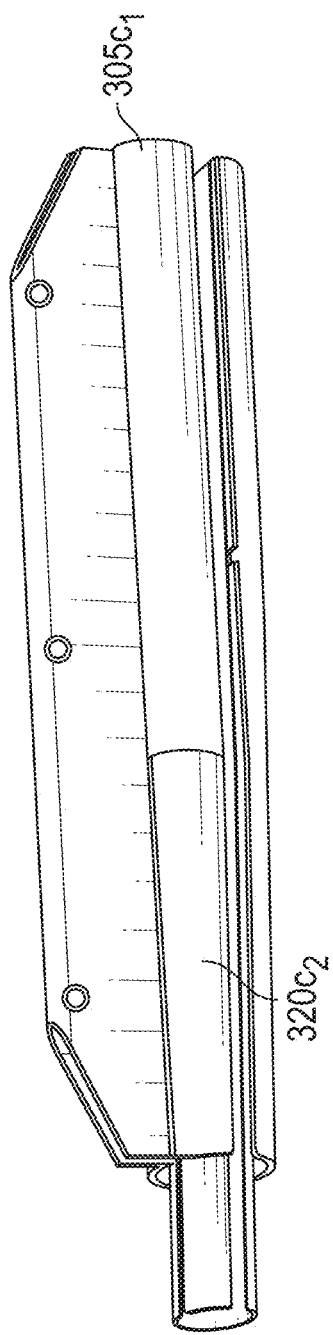

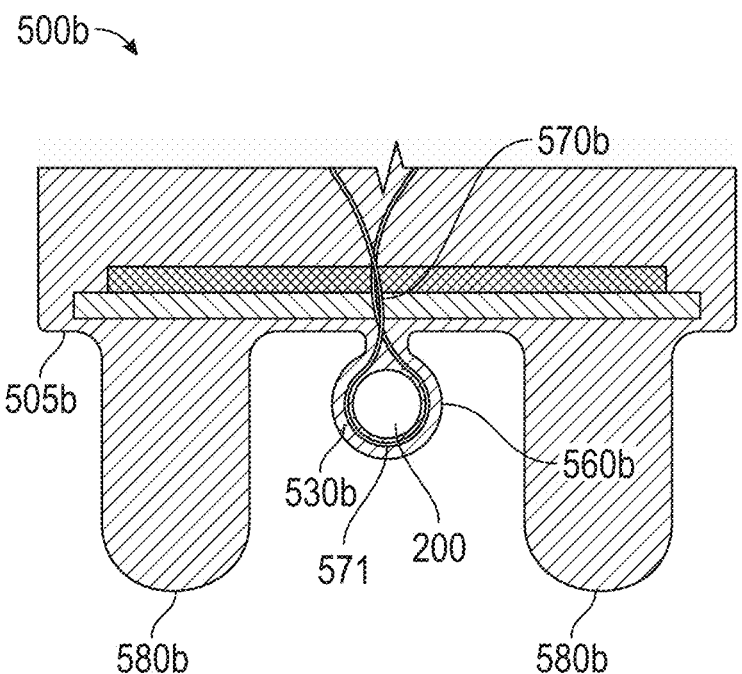
FIG. 16
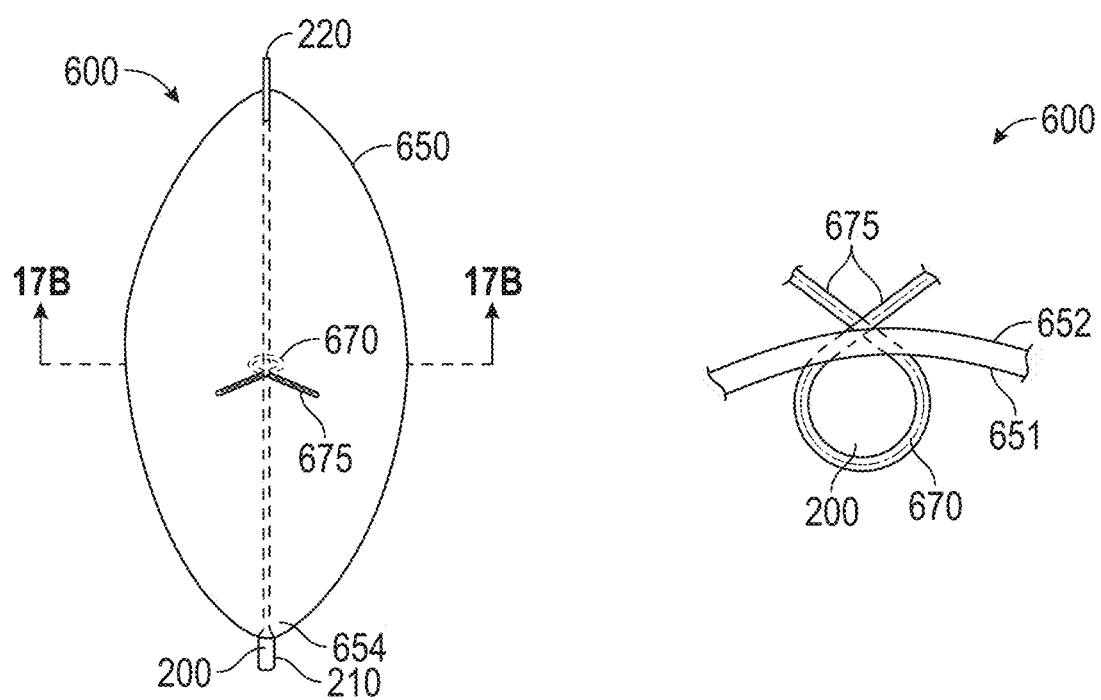
FIG. 17A
FIG. 17B

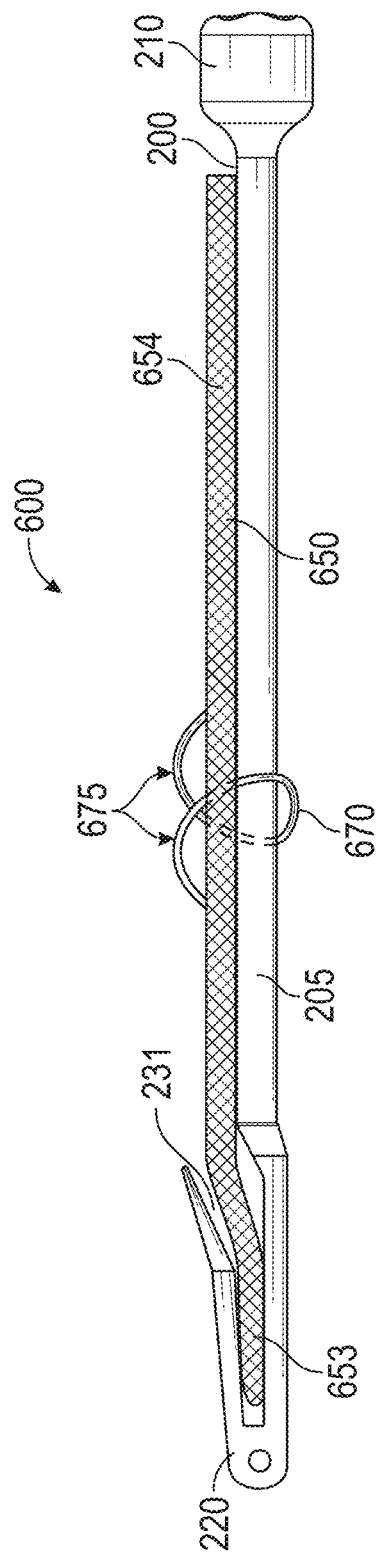

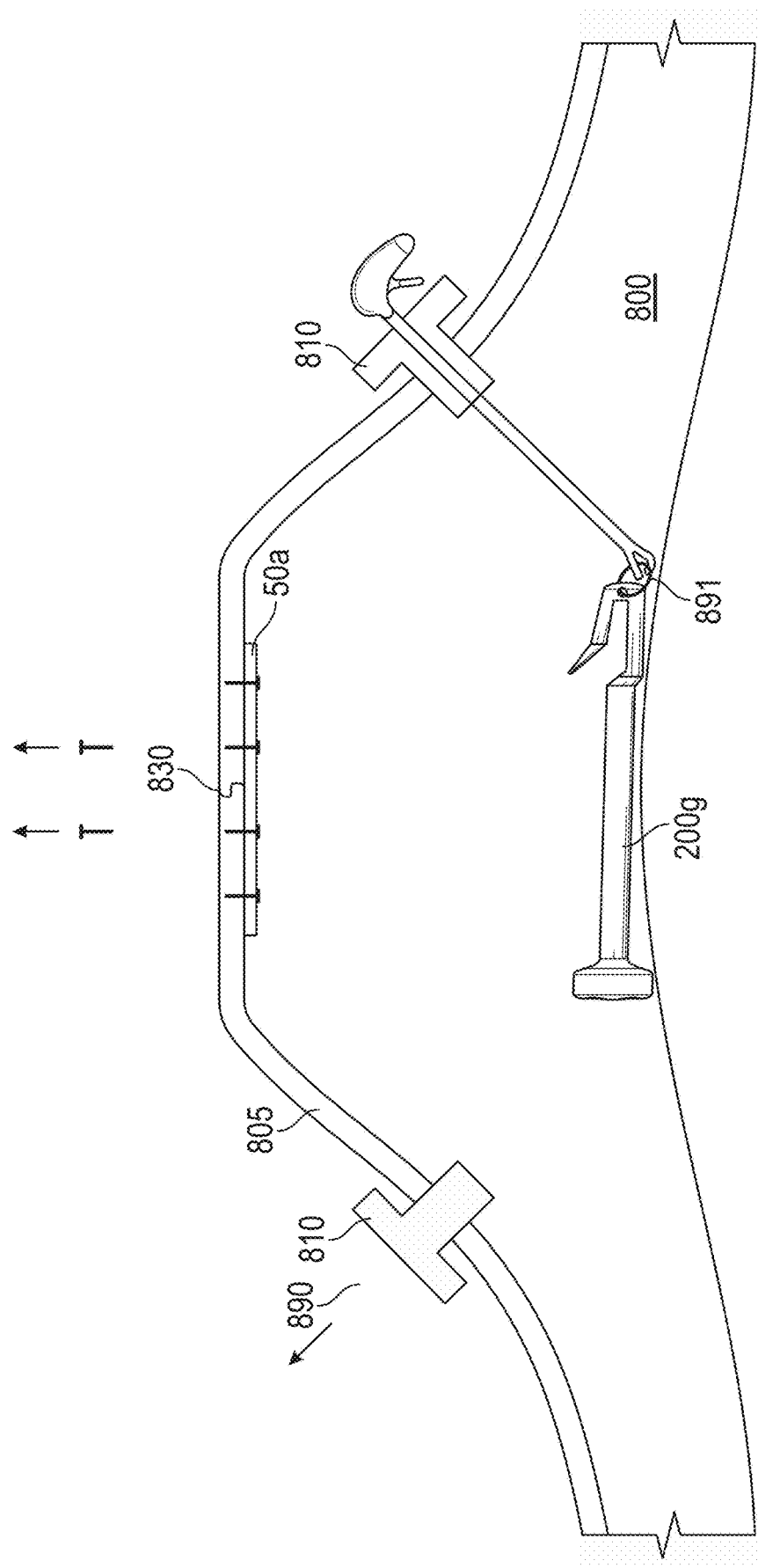

KITS FOR SURGICAL REPAIR OF SOFT TISSUE DEFECTS AND COMPONENTS, PACKAGING, AND METHODS OF USE THEREOF

CROSS-REFERENCE TO RELATED APPLICATIONS

This application claims the benefit of and priority to European Patent Application Number 20315213.7 filed on Apr. 23, 2020, the disclosure of the above-identified application is hereby incorporated by reference in its entirety.

TECHNICAL FIELD

The present disclosure describes kits for surgical repair of soft tissue defects, including hernias, and particularly to the components, packaging, and methods of use of such kits.

BACKGROUND

Various prosthetic repair materials are employed by surgeons for soft tissue repair including the repair of anatomical defects such as tissue and muscle hernias. For example, a ventral hernia in the abdominal wall is commonly repaired using an implantable sheet of biocompatible fabric, such as a knitted mesh (PARIETEX™, VERSATEX™, and the like) or a composite fabric that includes a mesh and an adhesion resistant barrier (SYMBOTEX™, PARIETENE™, and the like). The fabric can be sutured, stapled, tacked, glued, or otherwise anchored in place over, under or within the defect. Tissue integration with the fabric, such as tissue ingrowth into and/or along the mesh fabric, eventually completes the repair. An implantable sheet of adhesion resistant material, if provided alone or in combination with a fabric, prevents the growth of fibrous adhesions between the bowel (and other organs located in the abdominal cavity) and the sheet or fabric, specifically when the sheet is implanted inside the cavity (i.e. under the defect).

Various surgical techniques may be employed for soft tissue repair, including open or laparoscopic procedures. In addition, these surgical techniques may be performed directly by surgeon or with the assistance of a surgical robot. During a laparoscopic procedure, the prosthetic fabric may be routed, directly by the surgeon or with the assistance of a surgical robot, to the surgical site through a slender laparoscopic or robotic cannula. The fabric is typically collapsed, such as by rolling or folding, into a reduced configuration to facilitate its passage through the narrow cannula. Certain repairs, such as laparoscopic repair of ventral hernias, may require large sheets of prosthetic fabric that may be difficult to deliver laparoscopically, as well as difficult to properly deploy, orientate, position, or fixate following delivery.

Preparation and/or delivery of the prosthetic fabric can critically impact later steps of the surgical procedure. In laparoscopic procedures, prosthetic fabrics are typically prepared and delivered into a small operating space. This can make the deployment, orientation, positioning, and/or fixating of the fabric more difficult and more time consuming. It can also require the surgeon to dedicate one hand to simply trying to maintain the fabric in a certain position while the surgeon's second hand is trying to fixate the fabric in the tissue. This can be particularly challenging since the edges of the fabrics tend to bend or fold inside the small workspace. Mispositioning of the fixated prosthetic fabric can potentially lead to hernia recurrence.

It is an object of the present disclosure to provide kits and/or components of a kit which are designed to make preparation, insertion, deployment, orientation, positioning, and/or fixation of an implantable sheet easier, more intuitive and less time-consuming thereby rendering the surgical procedure more efficient and more effective.

It is another object of the present disclosure to provide kits and/or components of a kit which are designed to be prepared or delivered in a manner which allows a surgeon, either directly or with the assistance of a surgical robot, to dedicate multiple hands to handle, deploy, orientate, position, and/or fixate the implantable sheet, during a conventional laparoscopic or a robotically assisted ventral hernia repair.

SUMMARY

Surgical kits for soft tissue defect repair are described herein. The surgical kits include a combination of components selected from an implantable sheet, a central tie, a delivery tool, a rolling device, and/or an insertion member.

In some embodiments, the delivery tool includes a flexible rod having an elongate body extending between a shaped proximal end portion and a distal end portion. The distal end portion includes a suture aperture defined therethrough, the suture aperture configured to receive a looped suture. The distal end portion also includes an attachment clip, the attachment clip positioned proximal to the suture aperture and including a slot defined within the distal end portion which extends longitudinally along a length of the distal end portion. The attachment clip is configured to secure a portion of the implantable sheet to the distal end portion of the delivery tool.

In embodiments, the rolling device includes a tubular body defining a channel therein. The tubular body also includes a first slit which extends along a length of the tubular body and is in communication with the channel. A handle opening is defined within a portion of the tubular body and is configured to receive a tie handle of a central tie therein. The channel may be circular or conical. The rolling device may further include a spout, a flange, and/or a fin.

In embodiments, a surgical kit is described including an implantable sheet having a central tie passing therethrough, the central tie forming a loop extending from a bottom side of the implantable sheet and a tie handle positioned on a top side of the implantable sheet. The kit also includes a flexible delivery tool including an elongate body extending between a shaped proximal end portion and a distal end portion, the distal end portion includes a clip attachment configured to secure a portion of the sheet therein. The clip attachment includes a slot extending longitudinally along a length of the distal end portion. The surgical kit can be used for hernia repair.

In some embodiments, the implantable sheet is a surgical mesh and the kit includes a combination of components selected from a surgical mesh, a central tie, a mesh delivery tool, a mesh roller, and/or an insertion member.

In some embodiments, the mesh delivery tool includes a flexible rod having an elongate body extending between a shaped proximal end portion and a distal end portion. The distal end portion includes a suture aperture defined therethrough, the suture aperture configured to receive a looped suture. The distal end portion also includes a mesh attachment clip, the mesh attachment clip positioned proximal to the suture aperture and including a slot defined within the distal end portion which extends longitudinally along a length of the distal end portion. The mesh attachment clip is configured to secure a portion of the surgical mesh to the distal end portion of the mesh delivery tool.

In some embodiments, the mesh rolling device includes a tubular body defining a channel therein. The tubular body also includes a first slit which extends along a length of the tubular body and is in communication with the channel. A handle opening is defined within a portion of the tubular body and is configured to receive a tie handle of a central tie therein. The channel may be circular or conical. The mesh rolling device may further include a spout, a flange, and/or a fin.

In some embodiments, a surgical kit is described including an implantable mesh having a central tie passing therethrough, the central tie forming a tie loop extending from a bottom side of the implantable mesh and a tie handle positioned on a top side of the implantable mesh. The kit also includes a flexible mesh delivery tool including an elongate body extending between a shaped proximal end portion and a distal end portion, the distal end portion includes a mesh clip attachment configured to secure a portion of the mesh therein. The mesh clip attachment includes a slot extending longitudinally along a length of the distal end portion. The surgical kit can be used for hernia repair.

A package for a surgical kit is also described. The kit may include at least an implantable sheet, a central tie, and a flexible sheet delivery tool. The package includes a base having an area configured to receive an implantable sheet, and a first channel formed in the base below the area configured to receive the implantable sheet. The first channel extends beyond the area configured to receive the implantable sheet. The first channel is configured to receive a sheet delivery tool and widens on a proximal end thereof to form a mouth. The base further includes a recess formed therein. The recess crosses over the first channel and further includes at least one finger engagement recess on each side of the first channel.

In embodiments, a method of repairing a soft tissue defect is described. The method includes combining an implantable sheet, and a sheet delivery tool to form a sheet-tool assembly, preparing the sheet-tool assembly for insertion into a patient, inserting the sheet-tool assembly into a patient, deploying the sheet inside the patient, orientating and fine positioning the sheet inside the patient and withdrawing the delivery tool from the patient. The soft tissue defect can be a ventral hernia.

In embodiments, a method of combining an implantable sheet, a central tie, and a sheet delivery tool to form a sheet-tool assembly is described. The method includes passing a central tie through a central portion of an implantable sheet to form a tie loop extending from a bottom side of the sheet and a tie handle on a top side of the sheet, and positioning an elongate body of a flexible sheet delivery tool within the tie loop. The method may further include securing a distal portion of the sheet in a slot defined in distal end portion of the sheet delivery tool.

In embodiments, a method of preparing the sheet-tool assembly for insertion into a patient is described. The method includes passing the tie handle of the sheet-tool assembly through a handle opening defined in a sheet rolling device, pulling the tie handle to draw the sheet-tool assembly into a channel defined within the sheet rolling device, and rotating the sheet delivery tool inside the channel of the sheet rolling device to cause the implantable sheet to roll around an outer surface of the delivery tool to form a rolled sheet-tool assembly. The rolled sheet-tool assembly may be maintained within the sheet rolling device until insertion into a patient. The tie handle may be positioned around an outer perimeter of the rolled sheet in the rolled sheet-tool assembly. An insertion member may be attached to a proximal end portion of the sheet delivery tool prior to rotating the sheet and the insertion member may be used to cause the delivery device to rotate.

In embodiments, a method of inserting the rolled sheet-tool assembly into a patient is described. The method includes attaching a distal end of the sheet rolling device to a trocar extending from an inside of the patient's body, wherein the rolled sheet-tool assembly is positioned with the channel of the sheet rolling device, pushing the rolled sheet-tool assembly with an insertion member positioned on a proximal end of the delivery tool through the channel of the rolling device and through the trocar into the patient's body, and removing the insertion member from the rolled sheet-tool assembly.

In embodiments, a method of deploying the sheet inside the patient is described. The method includes introducing a suture catcher into the patient's body by penetrating through the center of the soft tissue defect from outside the patient's body, catching or grasping the tie handle of the central tie with the suture catcher, withdrawing the suture catcher and the tie handle back through the center of the tissue defect to the outside of the patient's body thereby releasing the rolled sheet of constraint by the tie handle and allowing the sheet to deploy, and securing the tie handle outside the patient's body thereby suspending the delivery tool beneath the tissue defect with the sheet therebetween and centered on the defect. With the sheet and delivery tool securely suspended, the sheet is automatically properly oriented, the sheet can be properly positioned and fixated to the tissue in or around the defect. In some embodiments, the suture catcher is a surgical device configured to catch or grab the suture handle, a non-limiting example of such a device includes an Endo Close® (Covidien LP, Mansfield, Mass.). The suture catcher may or may not include a needled end.

In embodiments, a method of withdrawing the delivery tool from the patient is described. The method includes inserting a surgical grasper through the trocar and into the patient's body, removing the distal end portion of the delivery tool from the sheet with the grasper, cutting the central tie allowing the delivery tool to separate from the sheet, grabbing the looped suture positioned on the distal end portion of the delivery tool with the grasper, and withdrawing the grasper attached to the delivery tool from the patient through the trocar. In embodiments, removal of the sheet from the distal end portion of the delivery tool can be performed by grabbing the looped suture positioned on the distal end portion of the delivery tool with the surgical grasper and pulling the delivery tool, via the looped suture, away from the sheet until the sheet is completely free of the tool. In some embodiments, the surgical grasper is a device configured to catch or grab the looped suture, a non-limiting example of such a device includes Endo Clinch® (Covidien LP, Mansfield, Mass.). In some embodiments, the suture catcher and the surgical grasper are the same device. In some embodiments, the suture catcher and the surgical grasper are different devices.

In some embodiments, a package for a surgical kit is also described. The kit may include at least an implantable mesh, a central tie, and a flexible mesh delivery tool. The package includes a base having an area configured to receive an implantable mesh, and a first channel formed in the base below the area configured to receive the implantable sheet. The first channel extends beyond the area configured to receive the implantable sheet. The first channel is configured to receive a mesh delivery tool and widens on a proximal end thereof to form a mouth. The base further includes a recess formed therein. The recess crosses over the first channel and further includes at least one finger engagement recess on each side of the first channel.

In embodiments, a method of repairing a soft tissue defect is described. The method includes combining an implantable mesh, and a mesh delivery tool to form a mesh-tool assembly, preparing the mesh-tool assembly for insertion into a patient, inserting the mesh-tool assembly into a patient, deploying the mesh inside the patient, orientating and fine positioning the mesh inside the patient and withdrawing the delivery tool from the patient. The soft tissue defect can be a ventral hernia.

In embodiments, a method of combining an implantable mesh, a central tie, and a mesh delivery tool to form a mesh-tool assembly is described. The method includes passing a central tie through a central portion of an implantable mesh to form a tie loop extending from a bottom side of the mesh and a tie handle on a top side of the mesh, and positioning an elongate body of a flexible mesh delivery tool within the tie loop. The method may further include securing a distal portion of the mesh in a slot defined in distal end portion of the mesh delivery tool.

In embodiments, a method of preparing the mesh-tool assembly for insertion into a patient is described. The method includes passing the tie handle of the mesh-tool assembly through a handle opening defined in a mesh rolling device, pulling the tie handle to draw the mesh-tool assembly into a channel defined within the mesh rolling device, and rotating the mesh delivery tool inside the channel of the mesh rolling device to cause the implantable mesh to roll around an outer surface of the delivery tool to form a rolled mesh-tool assembly. The rolled mesh-tool assembly may be maintained within the mesh rolling device until insertion into a patient. The tie handle may be positioned around an outer perimeter of the rolled mesh in the rolled mesh-tool assembly. An insertion member may be attached to a proximal end portion of the mesh delivery tool prior to rotating the mesh and the insertion member may be used to cause the delivery device to rotate.

In embodiments, a method of inserting the rolled mesh-tool assembly into a patient is described. The method includes attaching a distal end of the mesh rolling device to a trocar extending from an inside of the patient's body, wherein the rolled mesh-tool assembly is positioned with the channel of the mesh rolling device, pushing the rolled mesh-tool assembly with an insertion member positioned on a proximal end of the delivery tool through the channel of the rolling device and through the trocar into the patient's body, and removing the insertion member from the rolled mesh-tool assembly.

In embodiments, a method of deploying the mesh inside the patient is described. The method includes introducing a suture catcher into the patient's body by penetrating through the center of the soft tissue defect from outside the patient's body, catching or grasping the tie handle of the central tie with the suture catcher, withdrawing the suture catcher and the tie handle back through the center of the tissue defect to the outside of the patient's body thereby releasing the rolled mesh of constraint by the tie handle and allowing the mesh to deploy, and securing the tie handle outside the patient's body thereby suspending the delivery tool beneath the tissue defect with the mesh therebetween and centered on the defect. With the mesh and delivery tool securely suspended, the mesh is automatically properly oriented, the mesh can be properly positioned and fixated to the tissue in or around the defect. In some embodiments, the suture catcher is a surgical device configured to catch or grab the suture handle, a non-limiting example of such a device includes an Endo Close® (Covidien LP, Mansfield, Mass.). The suture catcher may or may not include a needled end.

In embodiments, a method of withdrawing the delivery tool from the patient is described. The method includes inserting a surgical grasper through the trocar and into the patient's body, removing the distal end portion of the delivery tool from the mesh with the grasper, cutting the central tie allowing the delivery tool to separate from the mesh, grabbing the looped suture positioned on the distal end portion of the delivery tool with the grasper, and withdrawing the grasper attached to the delivery tool from the patient through the trocar. In embodiments, removal of the mesh from the distal end portion of the delivery tool can be performed by grabbing the looped suture positioned on the distal end portion of the delivery tool with the surgical grasper and pulling the delivery tool, via the looped suture, away from the mesh until the mesh is completely free of the tool. In some embodiments, the surgical grasper is a device configured to catch or grab the looped suture, a non-limiting example of such a device includes Endo Clinch® (Covidien LP, Mansfield, Mass.). In some embodiments, the suture catcher and the surgical grasper are the same device. In some embodiments, the suture catcher and the surgical grasper are different devices.

BRIEF DESCRIPTION OF THE DRAWINGS

Various embodiments of the kits and/or components are described herein with reference to the drawings wherein:

FIGS. 2A-2B are perspective views of a mesh delivery tool described in at least one embodiment herein;

FIG. 3A is a side view of a mesh delivery tool described in at least one embodiment herein;

FIG. 3B is an end view of the mesh delivery tool depicted in FIG. 3A and described in at least one embodiment herein;

FIG. 4A is a side view of a mesh delivery tool described in at least one embodiment herein;

FIGS. 4B-4C are side views of various distal end portions of a mesh delivery tool described in at least one embodiment herein;

FIG. 5A is a side view of a mesh delivery tool in a unidirectional configuration as described in at least one embodiment herein;

FIG. 5B is a top view of the mesh delivery tool depicted in FIG. 5A in a multidirectional configuration as described in at least one embodiment herein;

FIG. 6C is a top view of the mesh delivery tool depicted in FIGS. 6A-6B in a generally unidirectional configuration as described in at least one embodiment herein;

FIGS. 7A and 7B include a side view and a top view of a mesh delivery tool in a unidirectional configuration as described in at least one embodiment herein;

FIGS. 7C-7E are top views of the mesh delivery tool depicted in FIGS. 7A-7B in various multidirectional configurations as described in at least one embodiment herein;

FIGS. 11A-11C include a side view, an end view, and a perspective view, respectively, of a mesh rolling device described in at least one embodiment herein;

FIG. 16 is a cross-sectional view of a package described in at least one embodiment herein;

FIGS. 17A-17C include a top view, and end view, and a side view, respectively of a mesh-tool assembly described in at least one embodiment herein;

FIGS. 19A-19E are cross-sectional schematic views of a method of using the kits and/or components described herein in treating a soft tissue defect as described in at least one embodiment herein.

DETAILED DESCRIPTION

The present disclosure describes a kit suitable for repairing various soft tissue defects, and particularly for repairing various types of hernias. The kit can include any of the following components, individually or in any combination: an implantable sheet; a central tie, a flexible delivery tool, a rolling device, and an insertion member. In some embodiments, the kits described herein may include at least an implantable mesh, a central tie, and a flexible mesh delivery tool configured to be secured or clipped to a portion of the implantable mesh. Such kits may further include a mesh rolling device, an insertion member, or both.

In some embodiments, the kits include an implantable mesh including a central tie extending therefrom, a flexible mesh delivery tool, a mesh rolling device, and an insertion member.

The present disclosure further describes packaging for any of the kits and/or the individual components of the kits described herein. As well as methods of treating or repairing various soft tissue defects or hernias utilizing any of the kits and/or components described herein. Methods of preparing, inserting, orienting, deploying, and/or fixating of an implantable sheet, such as an implantable mesh, using the various components described herein are also provided.

Figure 1:
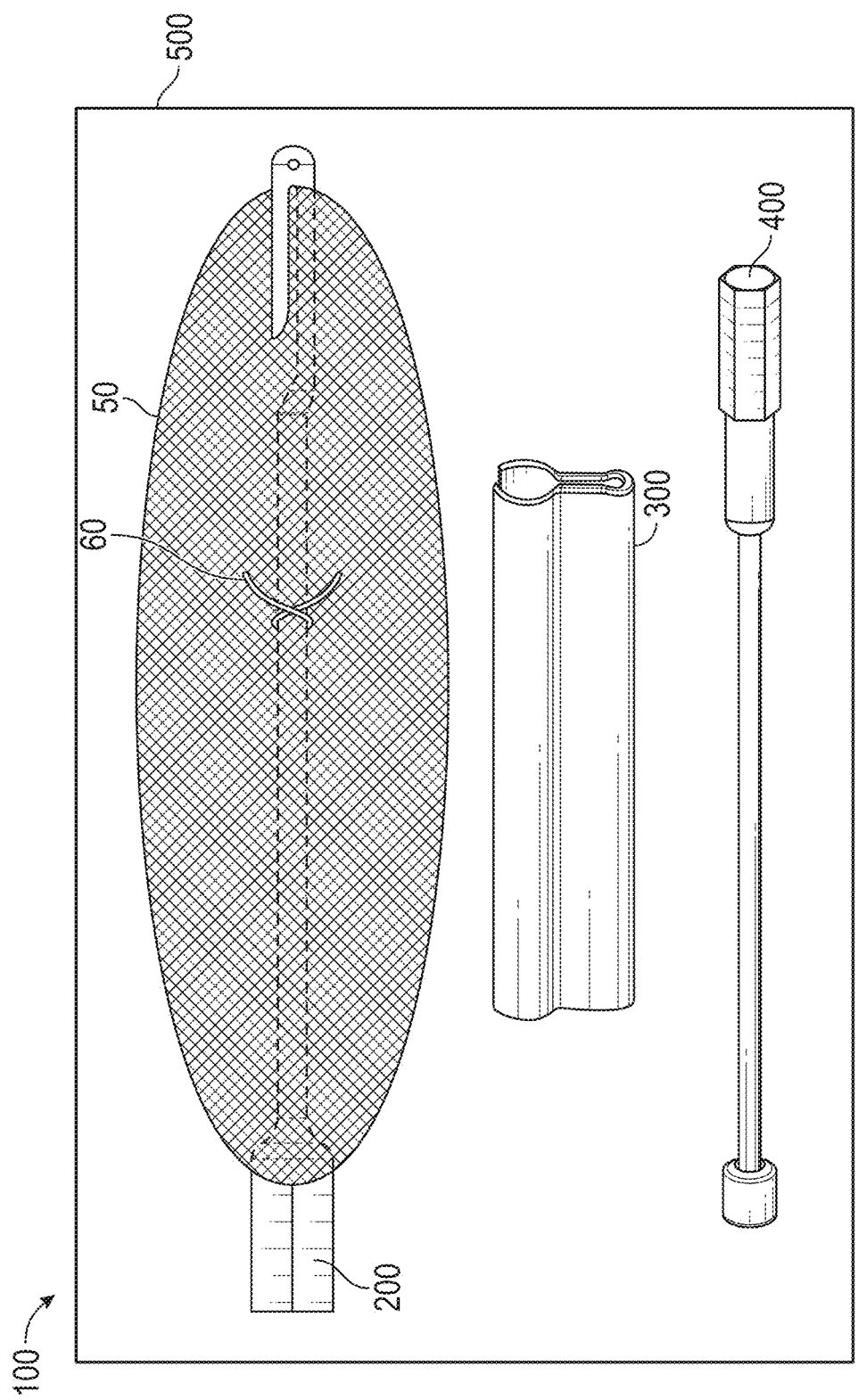
FIG. 1 is top view of a kit described in at least one embodiment herein.

In FIG. 1, a kit 100 as described in at least one embodiment herein is depicted. The kit 100 includes at least an implantable sheet 50 and a delivery tool 200. The kit 100 is shown being positioned or stored in a package 500 and further including a rolling device 300, an insertion member 400, and a central tie 60 extending from the sheet 50. Each of these components are provided in more detail hereinbelow.

I. Implantable Sheet

By implantable, the sheets described herein are configured to be positioned at a location within a body for any sufficient amount of time to at least temporarily treat and/or repair a soft tissue defect. In some embodiments, the biocompatible sheet is configured to be located within a portion of the abdominal cavity.

The implantable sheets described herein can be generally planar and may include any biocompatible porous or non-porous material configured to treat and/or repair a soft tissue defect. Some non-limiting examples of suitable sheets include surgical mesh, tissue scaffolds, adhesion barriers, surgical slings, surgical foams, and combinations thereof. The implantable sheet may be woven, non-woven, knitted, braided, cast, extruded, pressed, lyophilized, and the like. The implantable sheet can be bioresorbable, partially bioresorbable or non-bioresorbable.

In some embodiments, the implantable sheets described herein are surgical mesh. In the context of this application the term "mesh", "surgical mesh", or "implantable mesh" refers to an arrangement of biocompatible filaments or yarns, for example a knitted material or woven or nonwoven fibrous material, arranged in a manner to include pores within the mesh face that can encourage tissue ingrowth. The mesh can be bioresorbable, partially bioresorbable or non-bioresorbable. The mesh is generally planar or includes at least a portion which is generally planar. The mesh includes first and second opposite faces and an outer perimeter which defines a center of the mesh on each face. The mesh is also flexible enough to be rolled onto the exterior of the mesh delivery tool and upon itself prior to insertion into a patient or a cavity defined within of a patient. The mesh can be produced from one or more layers of fabric and may optionally include an anti-adhesion barrier layer positioned on at least one portion or one side of the fabric thereby forming a composite mesh. Such meshes are well known to the person skilled in the art. The mesh can also be provided in any shape (rectangular, square, circular, oval, etc.) and size. In some embodiments, the mesh may be round or elliptical in shape when unrolled.

The implantable mesh may be a two-dimensional knitted fabric or a three-dimensional knitted fabric. In the context of the present application, the expression "two-dimensional knitted fabric" means a knitted fabric having two opposite faces linked together by stitches but having no spacers imparting a certain thickness to it: such a knitted fabric may be obtained, for example, by knitting threads on a warp or Raschel knitting machine using two guide bars. Examples of two-dimensional knitted fabrics suitable for the present invention are given in the document WO2009/071998.

In the present application, the expression "three-dimensional knitted fabric" means a knitted fabric having two opposite faces linked together by spacers imparting a significant thickness to the knitted fabric, said spacers consisting of connecting threads additional to the threads forming the two faces of the knitted fabric. Such a knitted fabric may be obtained, for example, using a double-bed Raschel knitting machine or warp knitting machine with a plurality of guide bars. Examples of knitting three-dimensional knitted fabrics suitable for the present invention are given in the documents WO99/05990, WO2009/031035, WO2009/071998.

Additionally, meshes within the scope and context of this disclosure may include fibrous biologic materials such as allografts (i.e., AlloDerm® Regenerative Tissue Matrix from Allergan), autografts, and xenografts (i.e., PERMACOL™, from Medtronic).

In some embodiments, the implantable sheets described herein are configured for use in minimally invasive surgical procedures. In some embodiments, the implantable sheets described herein are configured for use with surgical techniques including, but not limited to, TAPPS (transabdominal preperitoneal surgery), TEPS (totally extraperitoneal surgery) or IPOM (intra peritoneal onlay mesh) techniques.

In particularly useful embodiments, the implantable sheet is a surgical mesh or composite surgical mesh suitable for repairing a ventral hernia. In particularly useful embodiments, the implantable sheet is a surgical mesh or composite surgical mesh suitable for repairing a ventral hernia using any appropriate surgical technique, including but not limited to TAPPS, TEPS, or IPOM techniques.

II. Central Tie

Each of the implantable sheets described herein, and particularly the implantable surgical meshes described herein, may further include a central tie positioned on or near a center of at least one of the two faces of the sheet. In some embodiments, the central tie is positioned on or near a center of both faces of the implantable sheet.

The central tie is designed to form at least one loop on a first side of the implantable sheet and at least one handle on a second opposite side of the sheet. The at least one tie loop configured to receive the delivery tool therethrough. The at least one tie handle configured to have a length sufficient to be manipulated from outside the body.

The central tie can made of any absorbable or nonabsorbable material and has a length greater than its width. For example, the central tie can be in the form of a suture, a fiber, a cable, a chord, a chain, a strip, a ribbon, a tether, a strap, or a long thin tubular mesh.

In some embodiments, the central tie is formed from one suture passing through both sides of the sheet to form the tie loop and the tie handle. In some embodiments, the central tie is formed from two or more sutures wherein at least a first suture forms the tie loop and the second suture forms the tie handle. The suture can be bioresorbable, partially bioresorbable or non-bioresorbable. The suture can be barbed or non-barbed. The suture can be armed or unarmed on the ends of the suture handle.

The central tie, when combined with the implantable sheet, passes through the sheet on a first bottom side to form at least one central tie loop extending therefrom. The central tie also passes through the sheet on a second opposite top side to form at least one, and in some instances two or more, handle(s) positioned on and extending from the second opposite top side of the sheet. The loop of the central tie extends away from the first bottom face of the sheet in a manner suitable to allow the flexible delivery tool to pass through the loop beneath the sheet. The central tie loop can be of sufficient size to act as an intermediary between the sheet and the delivery tool to indirectly connect the flexible delivery tool to the sheet without necessarily directly contacting the sheet. The tie loop allows a portion of the delivery tool to be suspended from a portion of the sheet via the extended loop. In some embodiments, the tie loop can be preformed in the central tie. In some embodiments, the central tie is woven or laced around itself to form the tie loop.

In embodiments wherein the sheet includes an anti-adhesion barrier on at least a central portion thereof, the central tie may also pass through the barrier.

On the second opposite top face, the central tie extends from the sheet a length sufficient to form a tie handle configured to be passed from the inside of the patient to the outside of the patient. In some embodiments, the tie handle is simply formed by the end(s) of the one or more ties extending from the second opposite face. In some embodiments, the central tie forms two handles extending from the second top face of the implantable sheet.

The tie handle is also designed to assist with preparing the sheet for rolling in rolling device, as well as making it simpler to center the sheet on the defect prior to deployment.

In some embodiments, the central tie is added to the sheet prior to packaging and/or during the manufacturing process of the sheet. In some embodiments, the central tie may be stored separately in the kit or package and can be added to the sheet by the surgeon after the package is open. In still other embodiments, the central tie may be a suture packaged separately from the sheet and added to the sheet by the surgeon immediately prior to implantation.

III. Delivery Tool

The kits described herein can include a delivery tool alone or in combination with at least the implantable sheet and the central tie. Some other kits include a delivery tool alone or in any combination of the components described herein.

The delivery tool includes a flexible rod having an elongate body configured to adapt to the curvature of a cavity inside a patient's body, such as the abdominal cavity. By being flexible, the delivery tool will not cause damage to tissue or organs inside the patient in the event the tool comes into direct contact with tissues or organs located inside the patient's cavity, such as the abdominal wall or organs inside an abdominal cavity. In addition, the flexible nature of the delivery tool makes it easier for the tool to enter the distal end of a trocar located inside the cavity during the withdrawal or removal process of the surgical procedure. Although flexible, the delivery tool still maintains a rigidity sufficient to generally support an implantable sheet, such as a surgical mesh, on an outer surface thereof and in a rolled configuration thereon.

In some embodiments, the flexible delivery tool in its natural state is a straight or unbent rod with the proximal and distal end portions generally 180 degrees apart. In such embodiments, the flexible delivery tool may further include the ability to bend to a curvature of at least 120 degrees when stressed, while maintaining the ability to return to its naturally straight or unbent configuration upon removal of the stress. In some embodiments, the flexible delivery tool may further include the ability to bend to a curvature of at least 90 degrees when stressed, while maintaining the ability to return to its naturally straight or unbent configuration upon removal of the stress.

The delivery tool can be made of any biocompatible material displaying the appropriate flexibility characteristics. Some non-limiting examples of suitable materials include polyamides, polyaryl ether ketone (PAEK), acrylonitrile butadiene styrene (ABS), polyether ether ketone (PEEK), polyoxymethylene (POM), nitinol (NiTi), polyetherimide (PEI), polycarbonates (PC), and combinations thereof. In addition to being biocompatible the materials used to form the delivery tool can be compatible with injection molding manufacturing processes and also compatible with standard sterilization methods, such as EtO and gamma radiation.

Some non-limiting examples of the delivery tools are provided in FIGS. 2A-7B. In some embodiments, the delivery tool is unidirectional (FIGS. 2A-4C), in that the tool extends in only one direction or includes a single axis. In some embodiments, the delivery tool is multidirectional (FIGS. 5A-7B), in that the tool extends in more than one direction or includes more than one axis.

As shown in more detail in FIGS. 2A and 2B, the delivery tool 200 described herein includes a flexible rod including an elongate body 205 extending between a proximal end portion 210 and a distal end portion 220. The proximal end portion 210 is shaped or contoured and thicker than the elongate body 205. The proximal end portion 210 is configured to connect to a distal end portion of an insertion member (not shown in FIGS. 2A-2B). The shaped proximal end portion 210 is also configured to be used to roll or rotate the implantable sheet around the elongate body 205 of the tool 200 when a portion of the implantable sheet is secured to the distal end portion 220 of the tool 200. Once the sheet is rolled around the tool 200, the proximal end portion 210, alone or in combination with the insertion member, can also be used to manipulate the tool 200 in a distal direction through a trocar and into the patient or the abdominal cavity specifically.

The shaped proximal end portion 210 of the delivery tool 200 has a thickness $t_1$, i.e., diameter when round, greater than a thickness $t_2$ of the elongate body 205. The shaped proximal end portion 210 of the delivery tool 200 can include any suitable shape or contour. As provided in FIG. 2B, in some embodiments, the proximal end portion 210 may include a block or square-shaped design. In other embodiments, the proximal end portion may be round (FIG. 3A) or hexagonal (FIG. 4A). Other various shapes of the proximal end portion are also envisioned including, but not limited to, triangular shaped, pentagonal shaped, heptagonal shaped, octagonal shaped, star-shaped, cross-shaped, and the like.

In some embodiments, as shown in FIGS. 3A-3B, the proximal end portion 210a may be round or circular in shape and include an indentation 211a into a thickness of the proximal end portion 210. The indentation 211a is shown as generally square with rounded corners wherein the outer edge 212a of the indentation 211a further includes alternating sections of peaks 213a and valleys 214a creating a non-planar outer edge 212a of the indentation 211. The indentation 211a provides an additional position for the insertion member to interact and lock into place with when secured to the proximal end portion of the tool 200a. As further provided in more detail below, the distal end portion of the insertion member may include a protrusion configured to match or mirror the shape of the indentation 211a to further stabilize the connection between the two components (See FIGS. 13A-13B). The non-planar outer edge 212a of the indentation 211a further strengthens the interaction between the proximal end portion 210a of the tool 200a and the insertion member when attempting to manipulate or rotate the tool 200a.

In some embodiments, the shape of the indentation and the shape of the proximal end portion may be the same. In some embodiments, the shape of the indentation and the shape of the proximal end portion may be different.

As depicted, the indentation 211a may be generally square-shaped. However, other various shapes of the indentation 211a (or the matching protrusion on the insertion member) are also envisioned including, but not limited to circular-shaped, triangular-shaped, pentagonal-shaped, hexagonal-shaped, octagonal-shaped, star-shaped, cross-shaped, and the like.

Figure 3C:
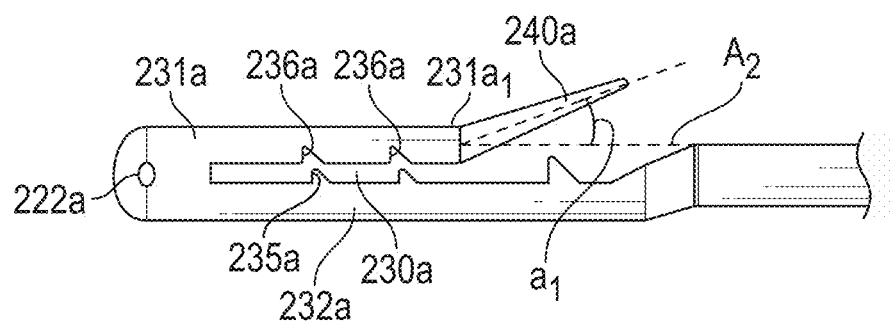
FIGS. 3C-3D are side views of various distal end portions of a mesh delivery tool described in at least one embodiment herein.
Figure 3D:
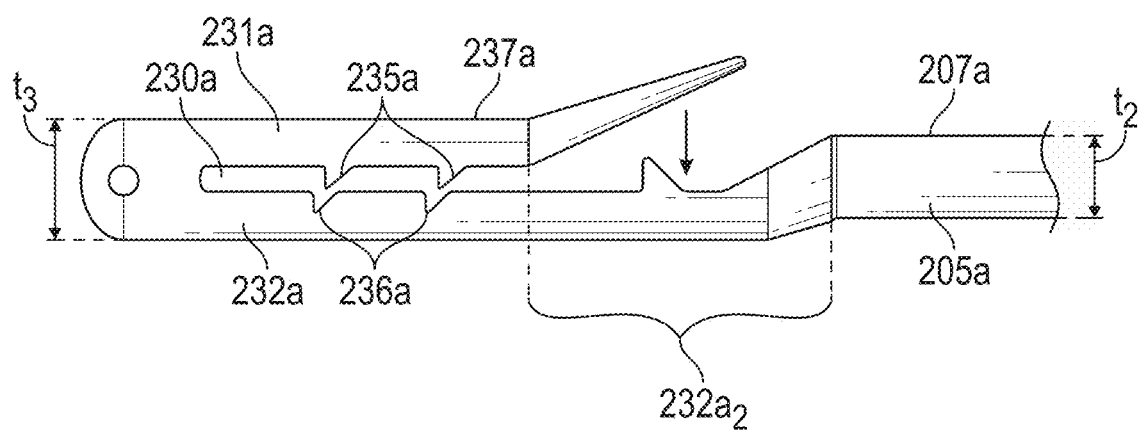

As further provided in more detail in FIGS. 3A and 3C-3D, the delivery tools described herein also include a distal end portion 220a which includes a suture aperture 222a configured to receive a looped material, such as suture or looped suture (not shown) therethrough and an attachment clip 225a configured to receive and secure a portion of the implantable sheet therein. The suture aperture 222a is positioned distal to the attachment clip 225a to ensure any suture passing through the suture aperture does not interfere with the attachment clip's ability to secure the implantable sheet therein. The suture aperture 222a is also positioned on the most distal portion of the delivery tool to make it easily accessible when inside the patient because the suture aperture 222a leads the way when the delivery tool is withdrawn from the patient. The suture or looped suture positioned within and extending from the suture aperture 222a also provides a larger target to grasp when trying to retrieve the delivery tool, as compared to the rounded distal end of the delivery tool without a suture or suture loop. In some embodiments the thickness $t_3$ of the distal end portion 220a is greater than the thickness $t_2$ of the elongate body 205a.

The attachment clip 225a includes a slot 230a extending longitudinally along a length of the distal end portion 220a dividing a part of the distal end portion 220a which is proximal to the suture aperture 222a into an upper jaw member 231a and a lower jaw member 232a. The implantable sheet, such as a surgical mesh, is intended to be received and secured within the slot 230a between the upper and lower jaw members 231a, 232a at some time prior to implantation, and particularly prior to preparing a sheet-tool assembly or mesh-tool assembly. In some embodiments, the attachment clip is sheet attachment clip. In some embodiments, the attachment clip is a mesh attachment clip.

As shown in FIGS. 3C-3D, in some embodiments, at least one of the upper or lower jaw members 231a, 232a may include at least one tooth or a plurality of teeth 235a extending therefrom into the slot 230a. In some embodiments, at least one of the upper or lower jaw members 231a, 232a may also include at least one recess 236a positioned across from and vertically aligned with a tooth 235a on the jaw member opposite the tooth 235a. The recess 236a being configured to receive a portion of the tooth 235a alone or in combination with a portion of the implantable sheet positioned therebetween when a sheet is secured within the slot 230a.

FIGS. 4A-4C depict additional embodiments of the delivery tool 200b including a proximal end portion 210b which is hexagonally shaped and includes a gap 215b positioned between first and second hexagonally shaped proximal end portions $210b_1$, $210b_2$. The gap 215b including a thickness $t_4$ less than the thickness $t_1$ of the proximal end portions $210b_1$, $210b_2$. In some embodiments, the thickness $t_4$ of the gap 215b is greater than or generally equal to the thickness $t_2$ of the elongate body 205.

FIGS. 4B-4C are directed to alternative embodiments of the distal end portion 220b of the delivery tool 200b. In FIG. 4B, in some embodiments, the slot 230b includes teeth 235a only on the upper jaw member 231b in a distal part of the slot 230b while the lower jaw member 232b in the distal part of the slot 230b remains generally flat. Still further in 4B, the lower jaw member 232b includes a tooth 235b in a proximal part of the slot 230b beneath the raised compound extension arm 240b. In FIG. 4C, the slot 230b defines a wavy or sinusoidal pathway through the distal end portion 220b of the delivery tool 200b. In each of the embodiments described herein, each of the teeth, recesses, and/or waves increase the surface area of the slot thereby increasing the surface area in contact with the implantable sheet when positioned in the slot. This increased surface area improves the hold strength of the distal end portion of the delivery tool on the sheet. The number of teeth, recesses, and/or waves can vary in number and location to optimize the hold strength of the delivery tool.

In addition to being configured to receive and retain a portion of the implantable sheet within the slot defined in the distal end portion of the delivery tool, the upper and lower jaw members are also flexible. The upper and lower jaw members can be made of the same flexible material which forms the elongate body. Therefore, the jaw members possess a naturally flexibility that can be used to more easily expand the space between the jaw members to remove the sheet from the slot. The jaw members also possess a natural flexibility which can be used to pinch the jaw members together when pressed upon thereby closing the slot with the sheet positioned therein.

As described in more detail hereinbelow, prior to insertion or implantation, the implantable sheet can be rolled around the delivery tool, and specifically the distal end portion of the delivery tool, while positioned within a rolling device. When the rolling occurs within the rolling device, pressure is applied to the upper and lower jaw members to pinch together or get closer narrowing the slot with the sheet positioned therein. This self-clamping effect is maintained while the sheet and delivery tool are maintained in the rolling device, as well as through the trocar during insertion. When removed from the rolling device or trocar, such as when the sheet and delivery tool are inserted into a patient's body, the additional pressure is removed and the self-clamping effect is diminished allowing the upper and lower jaw members to start to return back to their natural spaced-apart position.

To further enhance the self-clamping effect, the distal end portion of the delivery tool may further include some additional pressure enhancing structures. For example, in some embodiments, the proximal end 231$a_1$, 231$b_1$ of the upper arm 231$a$ may include a raised tension arm 240$a$ (FIGS. 3C and 3D) or a raised compound tension arm 240$b$ (FIG. 4B) extending therefrom. In another example, in some embodiments, the distal end portion 220$b$ of the delivery tool 200$b$ may include crenulations 250$b$ extending outwardly from an outer surface 237$b$ of the upper jaw member 231$b$, the outer surface 247$b$ of the lower jaw member 232$b$, or an outer surface 207$b$ of the elongate body 205$b$ (FIGS. 4B and 4C).

In FIGS. 3C and 3D, the raised tension arm 240$a$ may extend in a generally proximal direction from a proximal end 231$a_1$ of the upper jaw member 231$a$ and at a first angle $a_1$ relative to a longitudinal axis $A_2$ of upper jaw member 231$a$. By being raised above the upper jaw member 231$a$ and the elongate body 205$a$, the raised tension arm 240$a$ will be a primary point of contact and pressure when the implantable sheet is rolled on an exterior of the delivery tool 200$a$. This pressure will force the upper jaw member 231$a$ closer to the lower jaw member 232$a$ narrowing the slot 230$a$ thereby enhancing the self-clamping effect between the delivery tool and the sheet.

As further depicted in FIGS. 3C and 3D, the raised tension arm 240$a$ extends a distance short of where the distal end portion 220$a$ meets the elongate body 205$a$. Because the upper jaw member 231$a$ may be shorter in length than the lower jaw member 232$a$, the raised tension arm 240$a$ may be positioned over a proximal end portion 232$a_2$ of the lower jaw member 232$a$. A tooth 235$a$ or recess 236$a$, of the same or larger size or proportion as those within the slot 230$a$, may be positioned on the raised tension arm 240$a$, the proximal end portion 232$a_2$ of the lower jaw member 232$a$, or both.

The first angle $a_1$ of the raised tension arm ranges from about 1 degree to about 60 degrees. In some embodiments, the first angle $a_1$ ranges from about 2 degrees to about 55 degrees. In other embodiments, the first angle $a_1$ ranges from about 3 degrees to about 50 degrees. In still other embodiments, the first angle $a_1$ ranges from about 5 degrees to about 45 degrees. In yet other embodiments, the first angle $a_1$ ranges from about 10 degrees to about 35 degrees.

In some embodiments, the first angle $a_1$ is less than or equal to about 60 degrees. In some embodiments, the first angle $a_1$ is less than or equal to about 45 degrees. In still other embodiments, the first angle $a_1$ is less or equal to about 35 degrees.

In FIG. 4B, in some embodiments, the proximal end 231$b_1$ of the upper jaw member 231$b$ includes a raised compound tension arm 240$b$ extending therefrom in a generally proximal direction and in a compound manner, in that the raised tension arm may extend in two or more planes. For example, as shown, a first portion 241$b$ of the raised compound tension arm 240$b$ extends at a first angle $a_1$ relative to a longitudinal axis $A_2$ of upper jaw member 231$b$ for a certain distance before a second portion 242$b$ of the raised compound tension arm 240$b$ extends at a second angle $a_2$ relative to an axis parallel to the longitudinal axis $A_2$ of the upper jaw member 231$a$. By being raised above the upper jaw member 231$b$ and/or the elongate body 205$b$, the raised compound tension arm 240$b$ will be a primary point of contact and pressure when the implantable sheet is rolled on an exterior of the delivery tool 200$b$. This pressure will force the upper jaw member 231$b$ closer to the lower jaw member 232$b$ narrowing the slot 230$b$ thereby enhancing the self-clamping effect between the delivery tool and the sheet. In addition, by extending in two or more planes, the raised compound tension arm more evenly distributes the added pressure across the length of the tension arm, as opposed to a single plane tension arm which tends to focus the added pressure at the point nearest the angle change.

As further depicted in FIG. 4B, the raised compound tension arm 240$b$ extends to the location where the lower jaw member 232$b$ and/or the distal end portion 220$b$ meets the elongate body 205$b$. Because the upper jaw member 231$b$ is shorter in length than the lower jaw member 232$b$, the compound raised tension arm 240$b$ may be positioned over a proximal end portion 232$b_2$ of the lower jaw member 232$b$. A tooth 235$b$ or recess, of the same or larger size or proportion as those within the slot 230$b$, may be positioned on the raised compound tension arm 240$b$, the proximal end portion 232$b_2$ of the lower jaw member 232$b$, or both.

The first angle $a_1$ of the first portion of the raised compound tension arm 240$b$ is similar to the first angle of raised tension arm. The first angle $a_1$ of the first portion of the raised compound tension arm can range from about 1 degree to about 60 degrees. In some embodiments, the first angle $a_1$ ranges from about 2 degrees to about 55 degrees. In other embodiments, the first angle $a_1$ ranges from about 3 degrees to about 50 degrees. In still other embodiments, the first angle $a_1$ ranges from about 5 degrees to about 45 degrees. In yet other embodiments, the first angle $a_1$ ranges from about 10 degrees to about 35 degrees.

The second angle $a_2$ of the second portion of the raised compound tension arm may be less than the first angle of the first portion of the raised compound tension arm. The second angle $a_2$ of the second portion of the raised compound tension arm can range from 0 degree to about 40 degrees. In some embodiments, the second angle $a_2$ ranges from about 1 degree to about 35 degrees. In other embodiments, the second angle $a_2$ ranges from about 2 degrees to about 25 degrees. In still other embodiments, the second angle $a_2$ ranges from about 5 degrees to about 20 degrees. In yet other embodiments, the second angle $a_2$ ranges from 0 degrees to about 10 degrees. In yet other embodiments, the second angle $a_2$ is 0 degrees. Although some of the various ranges described for the first and second angles may partially overlap, in some embodiments, the first and second angles may include any combination of their respective ranges or degrees described herein, within the context that the first angle is always higher than the second angle.

As further depicted in FIG. 4B, a length of the first part 241b of the raised compound tension arm 240b is less than a length of the second part 242b of the raised compound tension arm 240b. In some embodiments, the first portion 241b of the raised compound tension arm 240b can represent less than about 40% the total length of the raised compound tension arm 240b and the second portion 242b (including any additional third, fourth, fifth portions, etc.) of the raised compound tension arm 240b may represent more than about 40% of the total length of the raised compound tension arm 240b.

In FIG. 4B, as well as FIG. 4C, in some embodiments, the delivery tool 200b and particularly the upper jaw member 231b, the lower jaw member 232b, or both, can further include crenulations 250b on an outer surface thereof. Unlike teeth which extend into the slot defined between the upper and lower jaw members, crenulations 250b extend outwardly from at least one of the jaw members 231b, 232b. The crenulations 250b are configured to engage the implantable sheet, and particularly the pores of a porous implantable sheet such as a surgical mesh, during rolling to improve the ability of the delivery tool to tightly roll the sheet thereon. The crenulations 250b are shown as generally round and may include a point 251b at a tip thereof. It is envisioned that the crenulations can be of any shape useful for engaging the sheet during rolling.

Although shown on only one of the jaw members, it is envisioned that the crenulations may be on both jaw members and/or may be positioned on an outer surface of at least a portion of the elongate body of the delivery tool.

Examples of multi-directional delivery tools are provided in FIGS. 5A-7B. In some embodiments, the multidirectional delivery tools are configured to transition between a generally unidirectional configuration and a multidirectional configuration. In some embodiments, the multidirectional delivery tools are configured to be unidirectional any time prior to deployment of the implantable sheet so that the tool can be easily passed into the patient's body through a trocar. In some embodiments, the multidirectional delivery tools are configured to be multidirectional throughout.

In FIGS. 5A and 5B, the multi-directional delivery tool 200c includes an elongate body 205c which includes one or more pivotable arms 209c configured to pivot or rotate from a first aligned position wherein the arms are vertically aligned with the elongate body 205c (FIG. 5A) to a second transverse position wherein the arms rotate about ninety degrees to be perpendicular to the elongate body 205c (FIG. 5B). In some embodiments, the arms are pivoted or rotated manually by the surgeon inside the patient's body, using either standard laparoscopic or robotic instruments. In some embodiments, the arms maintain and display a nature bias to pivot or rotate away from the elongate body. In such embodiments, the combination of the rolling device, the rolled implantable sheet, and the central tie may be used, prior to insertion, to prevent the naturally biased arms from rotating or pivoting away from the elongated body prematurely.

As further depicted in FIGS. 5A and 5B, the one or more arms do not cross the center C of the elongate body because the central tie (not shown) may be located in this area when assembled with the implantable sheet. Although the central tie does not prevent the sheet from deploying because the tie passes through the sheet, the central tie does not pass through the delivery tool but rather surrounds the tool possibly preventing arms positioned across the center of the elongate body of the tool from being able to rotate or pivot. Also, premature removal of the central tie may render the delivery tool unable to suspend the sheet from tissue in a top portion of a patient's body cavity. So, in some embodiments, the one or more pivotable arms are configured to avoid the central tie and/or a central portion of the elongate body completely.

Figure 6A:
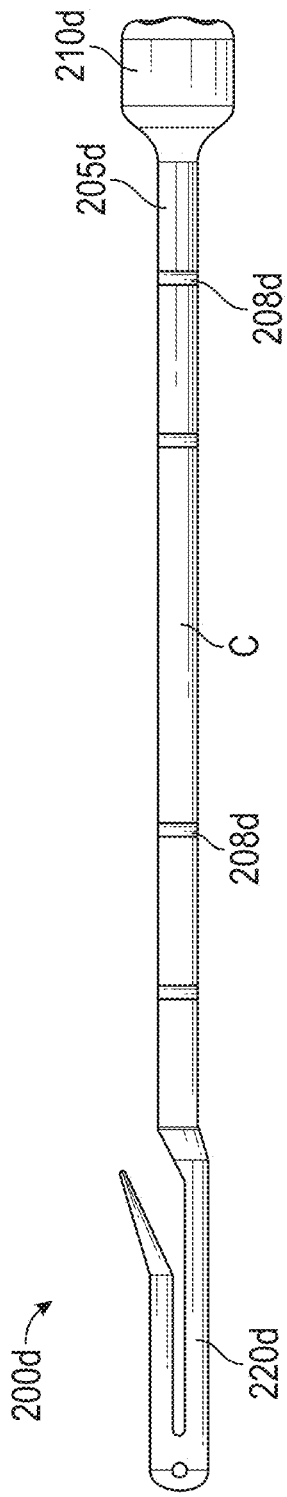
FIGS. 6A-6B include a side view and top view, respectively, of a multidirectional mesh delivery tool described in at least one embodiment herein.
Figure 6B:
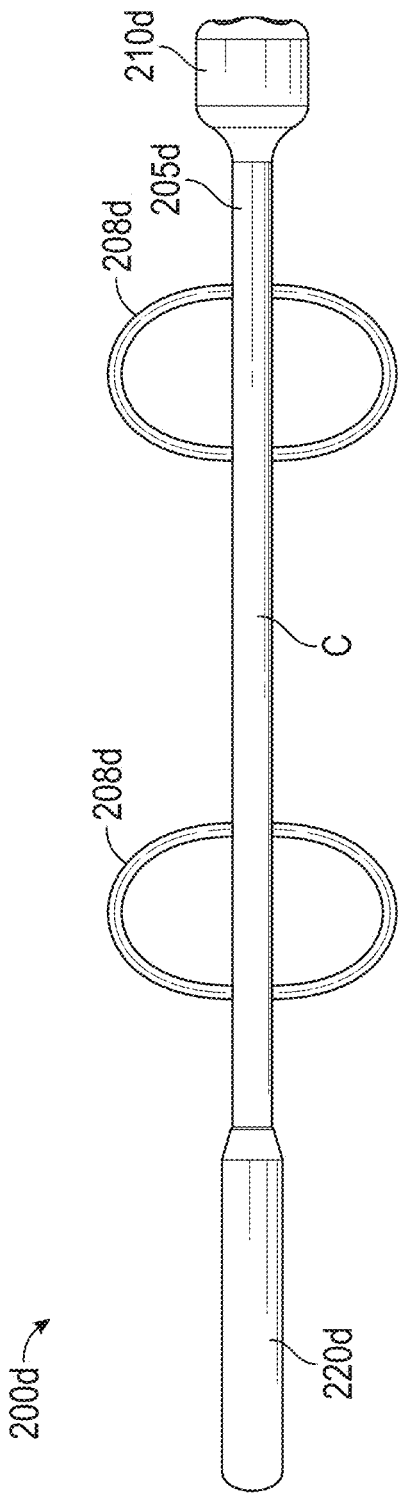

In FIGS. 6A-6C, the multidirectional delivery tool 200d includes resilient arms 208d extending from the elongate body 205d at two or more locations. Unlike the pivotable arms 209c in FIGS. 5A and 5B, the resilient arms 208d do not pivot or rotate about the elongate body 205d. Rather, the resilient arms 208d are generally designed to maintain the extended configuration shown in FIG. 6A whenever unrestrained. As depicted in FIG. 6C, in order to be received within the rolling device and/or pass through a trocar, the resilient arms 208d can be deformed, i.e., bent, folded, pressed, against the elongated body 205d to form a generally unidirectional configuration and to a size sufficiently small enough to fit and pass through the rolling device and/or the trocar. In addition, upon insertion into the patient, the resilient arms 208d are released from the restraints of the rolled implantable sheet, the rolling device, and/or the trocar walls to naturally return to their original expanded configuration (FIG. 6A). In some embodiments, the resilient arms 208d form rounded or elliptical arms affixed to and extending from the elongate body.

The resilient arms 208d can be made from any suitable material. Some non-limiting examples of suitable resilient materials include polyamides, polyaryl ether ketone (PAEK), acrylonitrile butadiene styrene (ABS), polyether ether ketone (PEEK), polyoxymethylene (POM), nitinol (NiTi), polyetherimide (PEI), polycarbonates (PC), and combinations thereof.

In FIGS. 7A-7E, the multidirectional delivery tool 200e includes an elongate body 205e configured to transition between a unidirectional configuration (FIGS. 7A-7B) and a multidirectional expanded configuration (FIGS. 7C-7E). In FIG. 7C, the elongate body 205e includes a slice 203e running a length of the elongate body 205e splitting the elongate body 205e into two pivotable parts $205e_1$, $205e_2$. The two pivotable parts $205e_1$, $205e_2$ connected to each other on both their ends 201e. Each pivotable part $205e_1$, $205e_2$ of the elongate body 205e includes a joint 202e designed to bend away from the slice 203e, and each other, thereby expanding the opening of the slice 203e. When straightened, the pivotable parts $205e_1$, $205e_2$ close the slice 203e to form the unidirectional configuration. In some embodiments, the pivotable parts $205e_1$, $205e_2$ of the elongate body 205e can be separated from each other or pivoted manually by the surgeon inside the patient's body, using either standard laparoscopic or robotic instruments. In some embodiments, the pivotable parts $205e_1$, $205e_2$ of the elongate body 205e maintain and display a nature bias to pivot away from each other. In such embodiments, the rolling device, the rolled implantable sheet, and/or the central tie may be used, prior to insertion, to prevent the naturally biased pivotable parts $205e_1$, $205e_2$ from pivoting away from each other prematurely.

In FIGS. 7D-7E, the elongate body 205*e* includes a plurality of curved or bent arms 209*d* which are configured to expand away from the elongate body 205*e*. In some embodiments, the curved or bent arms 209*d* maintain and display a natural bias to pivot away from the elongate body 205*e*. In such embodiments, the rolling device, the rolled implantable sheet, and/or the central tie may be used, prior to insertion, to prevent the naturally biased curved or bent arms 209*d* from pivoting away from the elongate body 205*e* prematurely.

In each of the delivery tools shown in FIGS. 7C-7E, the transition or expansion of the delivery tool occurs across the center C of the elongate body wherein the central tie may interfere with the transition. Therefore, in some embodiments, the kits which utilize such a multidirectional tool may include an implantable sheet having a central tie and one or more end ties. End ties, similar to the central ties, include a long, thin biocompatible material, such as a suture or ribbon, passed through the sheet to form a loop extending from a bottom side of the sheet and one or more handles positioned on a top opposite side of the sheet. The end ties being positioned on opposite ends of the sheet with the central tie positioned therebetween. The two end ties and the central ties being aligned in a straight row. Alignment of the ties allows the multidirectional tool to pass through each of the loops in the unidirectional configuration. As described in more detail below, to deploy the implantable sheet, the tie handles of the central tie can still be used to ensure proper centering on the tissue defect, however, a similar process can be used with the handles of the end ties to suspend the sheet and the delivery tool on opposite ends as well. Once suspended by the end ties, removal of the central ties is then no longer premature and the multidirectional tool will remain suspended beneath the tissue defect via the end ties when the tool transitions from an unidirectional configuration to a multidirectional configuration.

In some embodiments, the delivery tool is a sheet delivery tool. In some embodiments, the delivery tool is a mesh delivery tool.

IV. Rolling Device

The rolling devices described herein are configured to prepare the implantable sheet, such as a surgical mesh, and the delivery tool for insertion into a patient. The rolling device is used to wrap the sheet around an outer surface of the flexible delivery tool to render the sheet in a rolled configuration prior to insertion. The rolling device may also be used by a surgeon to transfer the delivery tool including the sheet in a rolled configuration to a trocar for insertion into a patient. The rolling device, unlike the implantable sheet and delivery tool, is not intended to be inserted into a patient.

Figure 8A:
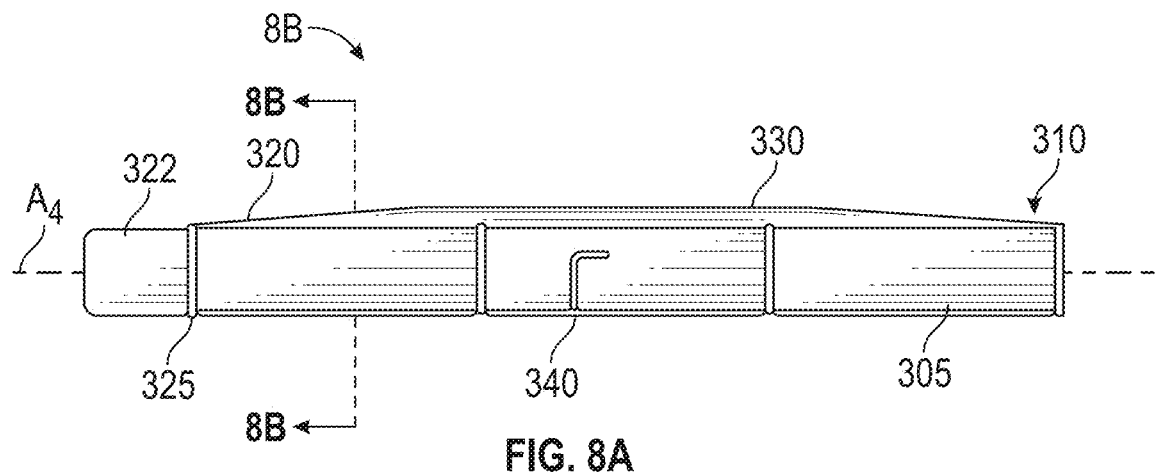
FIGS. 8A and 8B include a side view and an end view, respectively, of a mesh rolling device described in at least one embodiment herein.
Figure 8B:
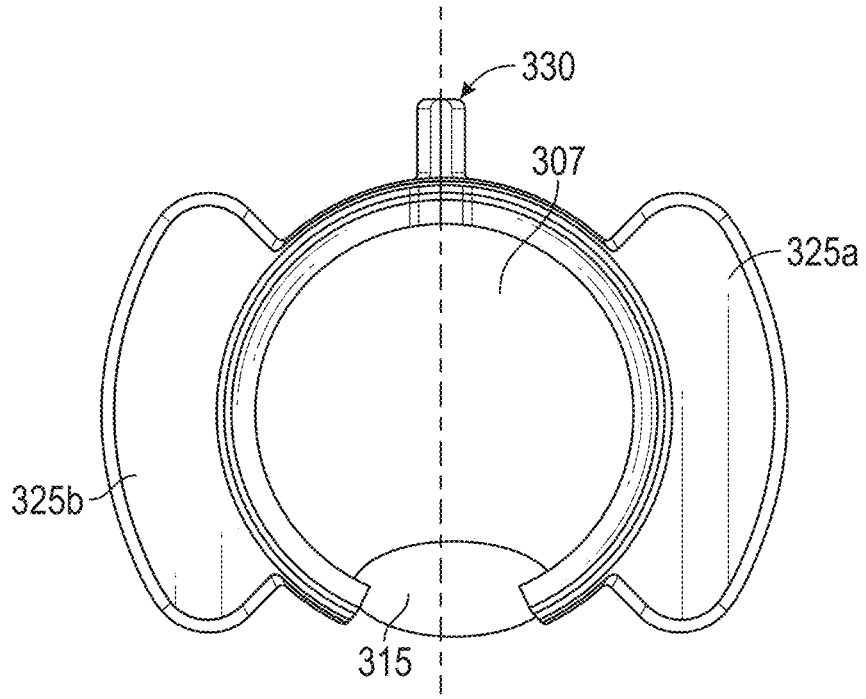

In FIGS. 8A-8B, a rolling device 300 is shown including a generally tubular body 305 extending between a proximal end portion 310 and a distal end portion 320 of the device 300, the tubular body 305 generally defines a channel 307 configured to receive both the implantable sheet and the delivery tool. The channel 307 extends the entire length of the tubular body 305 through both the proximal and distal end portions 310, 320 of the device 300. A first slit 315 also extends the entire length of the tubular body creating an open generally tubular body 305 and/or an open channel 307. At least one fin 330 also extends along a length of the tubular body 305 and on an outer surface of the tubular body 305. The rolling devices described herein further include at least one handle opening 340 configured to receive the handle of the central tie prior to rolling. In some embodiments, the tubular body 305 may have a C-shaped cross-section.

The first slit 315 is configured to allow passage of the sheet and delivery tool into the channel 307 of the tubular body 305. The first slit 315 also provides the rolling device 300, which can be made of a rigid or semi-rigid material, the flexibility to expand or contract along the slit 315 as needed to accommodate different sizes of the implantable sheet and/or the delivery tools.

The rolling device 300 further includes a spout 322 and at least one flange 325 extending from the distal end portion 320. The spout 322 extends from the distal end portion 320 along the longitudinal axis $A_4$ of the device 300 and is configured to fit within or mate with a trocar opening to allow access into the trocar during insertion of the sheet and/or delivery tool. The at least one flange 325 is positioned on the distal end portion 320 proximal to the spout 322 and extends generally perpendicular to longitudinal axis $A_4$ of the device 300. In some embodiments, the device 300 may include two flanges 325*s*, 325*b*, each positioned on opposite sides of the device 300. In some embodiments, the spout 322 can be designed as two separate half-circles, each positioned on opposite sides of the first slit 315.

As shown specifically in FIG. 8B, in some embodiments, the rolling device 300 includes a rigid fin 330 vertically aligned with, and in particular vertically centered on, the first slit 315. The device 300 may further include first and second flanges 325*a*, 325*b* positioned symmetrically on opposite sides of the fin 330. Also, the handle opening 340 may be defined within the outer wall of the tubular body 305 of the device 300 and may be generally L-shaped. Still further, as shown, the tubular body 305 can include a generally circular channel along the entire length of the device maintaining a generally constant diameter throughout.

Figure 9A:
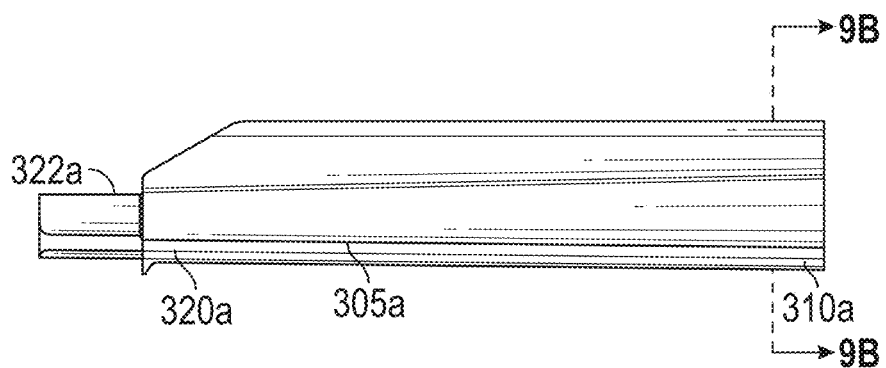
FIGS. 9A-9C include a side view, an end view, and a perspective view, respectively, of a mesh rolling device described in at least one embodiment herein.
Figure 9B:
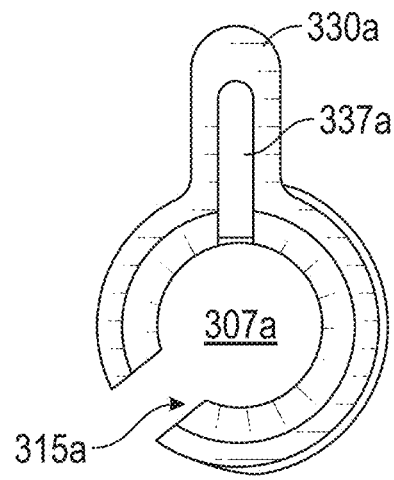
Figure 9C:
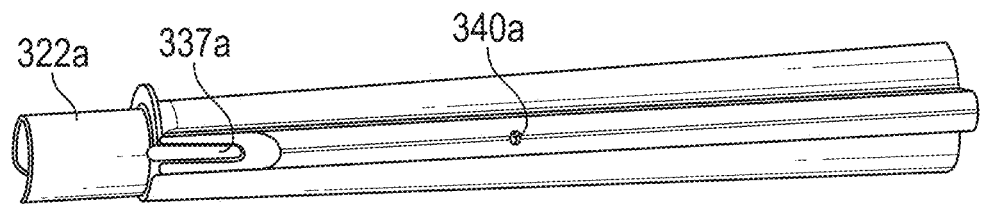

As shown in FIGS. 9A-9C, in some embodiments, the rolling device 300*a* includes a tubular body 305*a* having conical channel 307*a*, wherein the diameter of the channel 307*a* is widest at the proximal end portion 310*a* and narrows at the distal end portion 320*a* of the body 305*a*. The diameter of the tubular body 305*a* being narrowest near the spout 322*a*. The conical channel 307*a* has been shown to improve efficiency in rolling of the implantable sheet when the sheet is either elliptical in overall shape when laid flat or larger in length or width of about 20 centimeters.

In some embodiments, as further shown in FIGS. 9A-9C, the fin 330*a* defines a fin cavity 337*a* therein along at least a portion of the length of the fin 330*a*. The fin cavity 337*a* ends at the spout 322*a*. The fin 330*a* and/or the fin cavity 337*a* is not vertically aligned with the first slit 315*a*. The fin 330*a* and/or the fin cavity 337*a* is offset or at an obtuse angle to the first slit 315*a*. The fin 330*a* further includes a handle opening 340*a* depicted as a single hole located on and passing through a wall of the fin 330*a*, particularly at the peak of the fin 330*a*, which connects to the fin cavity 337*a*. The first hole 340*a* is configured to allow the handle of the central tie to pass vertically therethrough for loading of the sheet and the delivery tool through the first slit 315*a* and into the channel 307*a* of the rolling device 300*a*. The fin cavity 337*a* is configured to allow the handle of the central tie to pass horizontally therethrough when the rolled sheet and the delivery tool are moved or forced distally through the channel 307*a* to be inserted into the trocar.

Figure 10A:
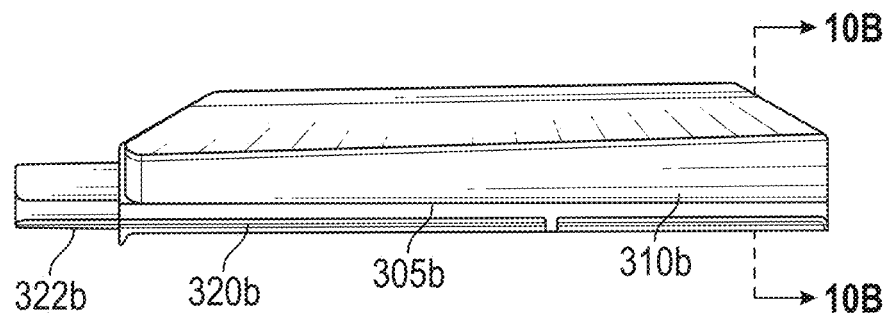
FIGS. 10A-10C include a side view, an end view, and a perspective view, respectively, of a mesh rolling device described in at least one embodiment herein.
Figure 10B:
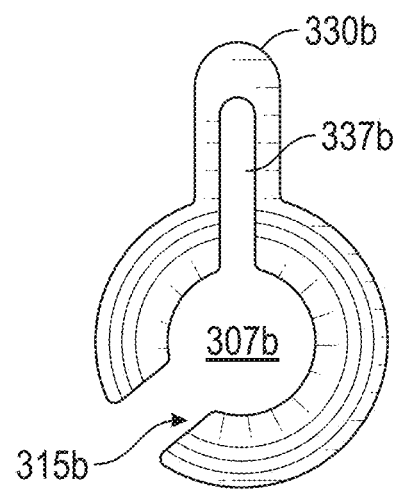
Figure 10C:
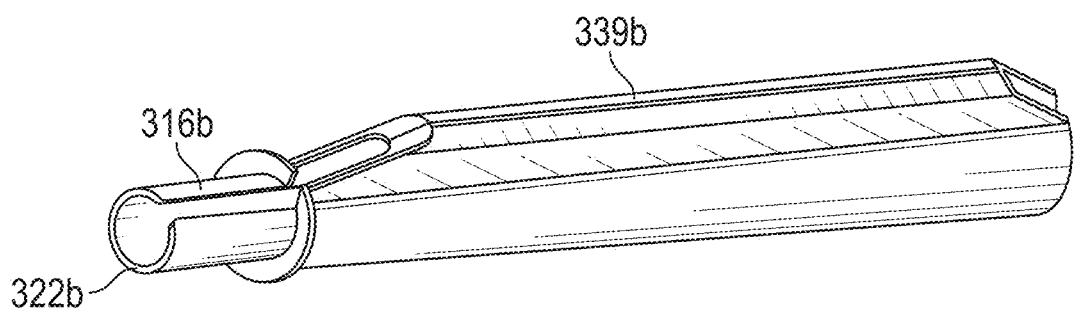

In some embodiments, as shown in FIG. 10A-10C, the fin cavity 337*b* does not end at the spout 322*b* but rather connects to a second slit 316*b* extending through the spout 322b. In addition, the fin cavity 337b extends through the peak of the fin 330b creating a fin groove 339b extending from the handle opening 340b distally towards the spout 322b. The fin cavity 337b, the fin groove 339b, and the second slit 316b of the spout 322b are all connected to allow the handle of the central tie to pass vertically and/or horizontally therethrough.

In FIGS. 11A-11C, in some embodiments, the tubular body 305c is both cylindrical in a first proximal part $305c_1$ and conical in second distal part $305c_2$. The first proximal part $305c_1$ includes a cylindrical shape wherein the diameter of the channel 307c remains constant and extends greater than or equal to 50% of the length of the elongate body 305c. The second distal part $305c_2$ includes the conical shape wherein the diameter of the channel changes, and particularly narrows. The conical part of the device extends 50% or less of the length of the elongate body 305c.

Figure 12:
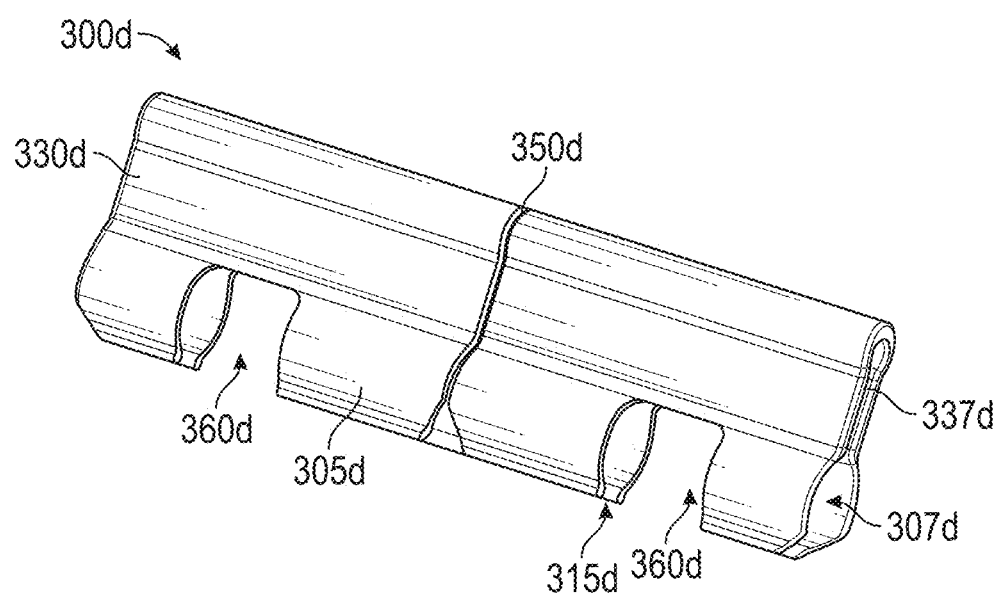
FIG. 12 is a perspective view of a mesh rolling device described in at least one embodiment herein.

In still other embodiments, as shown in FIG. 12, the rolling device 300d described herein may include a third slit 350d which extends vertically, generally perpendicular to the longitudinal axis of the channel 307d. The third slit 350d extends through a sidewall of the fin 330d and a sidewall of the tubular body 305d. By extending through one entire side of the device 300d, including the sidewalls of the tubular body 305d and the fin 330d, the handle of the central tie can be easily transferred into the inside of the device 300d for faster loading of the implantable sheet and the delivery tool into the channel 307d.

As further depicted in FIG. 12, in some embodiments, the elongate body and thus the channel 307d and first slit 315d are discontinuous and do not extend completely across the entire length of the device creating open spaces 360d between portions of the elongate body 305d. Also, in some embodiments, the rolling device may not include a spout or flange extending from a distal end portion thereof.

The fins as described herein are configured to be a handle for the surgeon to use when handling the rolling device. The fin cavities, of the fins described herein, participate in the global flexibility of the rolling device, to compress or relax the rolled sheet and delivery tool inside the channel for the rolling device.

The rolling device can be made of any suitable material. Some non-limiting examples include, but are not limited to, stainless steel, polycarbonate, polypropylene, polyethylene, polyether ether ketones, polyaryl ether ketones, polyamide, polyurethane, polyethylene terephthalate, polyethylene terephthalate glycol modified, acrylonitrile butadiene styrene, polyethylene high density, polyoxymethylene, and combinations thereof.

In some embodiments, the rolling device is a sheet rolling device. In some embodiments, the rolling device is a mesh rolling device.

In addition to the various rolling devices described hereinabove, in some embodiments, the rolling device is a rolling device described in any of U.S. Pat. Nos. 8,317,808; 8,734,473; 9,364,311; 10,052,126; and 10,016,265, each of which are incorporated herein by reference.

V. Insertion Member

The insertion members described herein are configured to connect or attach to the proximal end of the delivery tool. Once attached, the insertion members are designed to rotate the delivery tool causing the implantable sheet to wrap around the exterior of the delivery tool into a rolled configuration. Therefore, the insertion member provides a dual ability or function for both rolling and inserting of the implantable sheet and delivery tool.

Figure 13A:
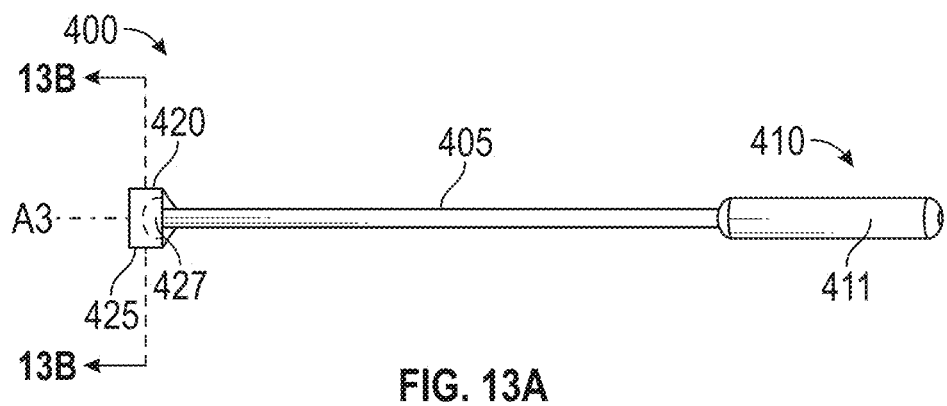
FIGS. 13A-13B include a side view and an end view, respectively, of an insertion member described in at least one embodiment herein.

FIG. 13A depicts an insertion member 400 having an elongate body 405 extending between a proximal end portion 410 and distal end portion 420 of the insertion member 400. The proximal end portion 410 of the insertion member 400 includes a handle or grip 411 designed to assist with moving the insertion member 400 longitudinally through the trocar and also with rotating of the insertion member 400 which in turn rotates the delivery tool inside the rolling device. The distal end portion 420 of the insertion member may include a socket 425 designed to mate with the proximal end portion of the delivery tool. The socket 425 including a socket cavity 426 having an inner perimeter which matches the outer perimeter of the shaped proximal end portion of the delivery tool. The socket cavity 426 may also include a socket protrusion 427 positioned within the cavity 426 which mates and/or properly sits within the indentation of the delivery tool. When attached, the insertion member 400 and the delivery tool share a common central longitudinal axis $A_3$. The insertion member 400 has a length that is longer than a typical trocar used for laparoscopic surgery. In some instances, the insertion member has a length that is longer than a trocar and a rolling device as described herein combined.

Figure 13B:
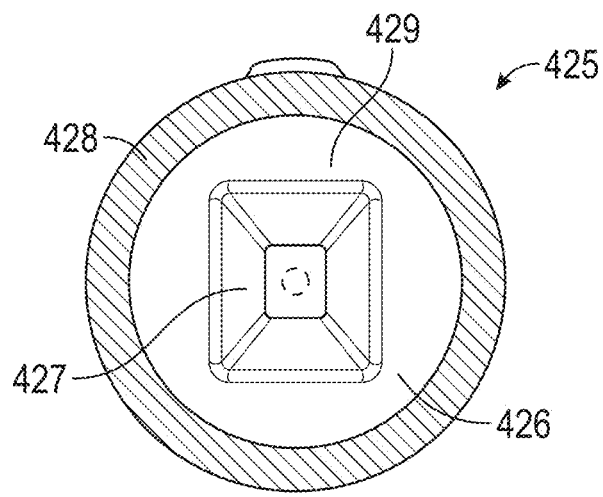

FIG. 13B shows an end view into the socket on the distal end portion 420 of an insertion member 400 along the longitudinal axis $A_3$. The socket 425 shown is configured to matingly engage with the circular shaped proximal end of FIG. 3B. The socket 425 includes a socket cavity 426 having a shape or contour which mirrors the shaped proximal end portion 210a of a delivery tool 200a. The socket cavity 426 including at least one sidewall 428 and a base 429 which together define the cavity 426. As shown, in some embodiments, the base 429 may further include a socket protrusion 427 configured to matingly engage an indentation carved into a proximal end of a delivery tool. The projection also having a shape or contour which mirrors the shape or contour of the indentation to ensure proper mating.

In some embodiments, the insertion member further includes an articulation means or articulation joint positioned along the elongate body between the socket and the handle. In some instances, the articulation means or articulation joint is positioned nearest the socket to best facilitate the separation of the insertion member from the flexible delivery tool by limiting a long over-center locking by the socket. In some embodiments, the articulation joint may allow passive articulation via a ball and socket joint which could locked by a locking collar slid over the joint thereby locking the member into a straight configuration, and when slid off the joint allowing the locking member to articulate.

The insertion member can be made of any suitable material. Some non-limiting examples include, but are not limited to, stainless steel, polycarbonate, polypropylene, polyethylene, polyether ether ketones, polyaryl ether ketones, polyamide, polyurethane, polyethylene terephthalate, polyethylene terephthalate glycol modified, acrylonitrile butadiene styrene, polyethylene high density, polyoxymethylene, and combinations thereof.

VI. Packaging

Each of the components and the various kits described herein are designed to be manufactured, stored, sold, transported and eventually used under sterile conditions. The present disclosure also provides a unique package suitable to maintain the sterility of the components and/or kits during each of these steps or events. The packages described herein are specifically designed to receive and store any combination of the components described herein in a manner which any or all of the components are secure and sterile but can be easily detached from the package with a minimal amount of direct touching or handling of the sterile implantable sheet, such as a surgical mesh, prior to implantation. In addition, the package is intended to allow the gathering of the components immediately prior to use or implantation while maintaining the least amount of direct human contact with the components that are actually positioned into the patient at the site of implantation, such as the implantable sheet, the delivery tool and/or the central tie.

Figure 14:
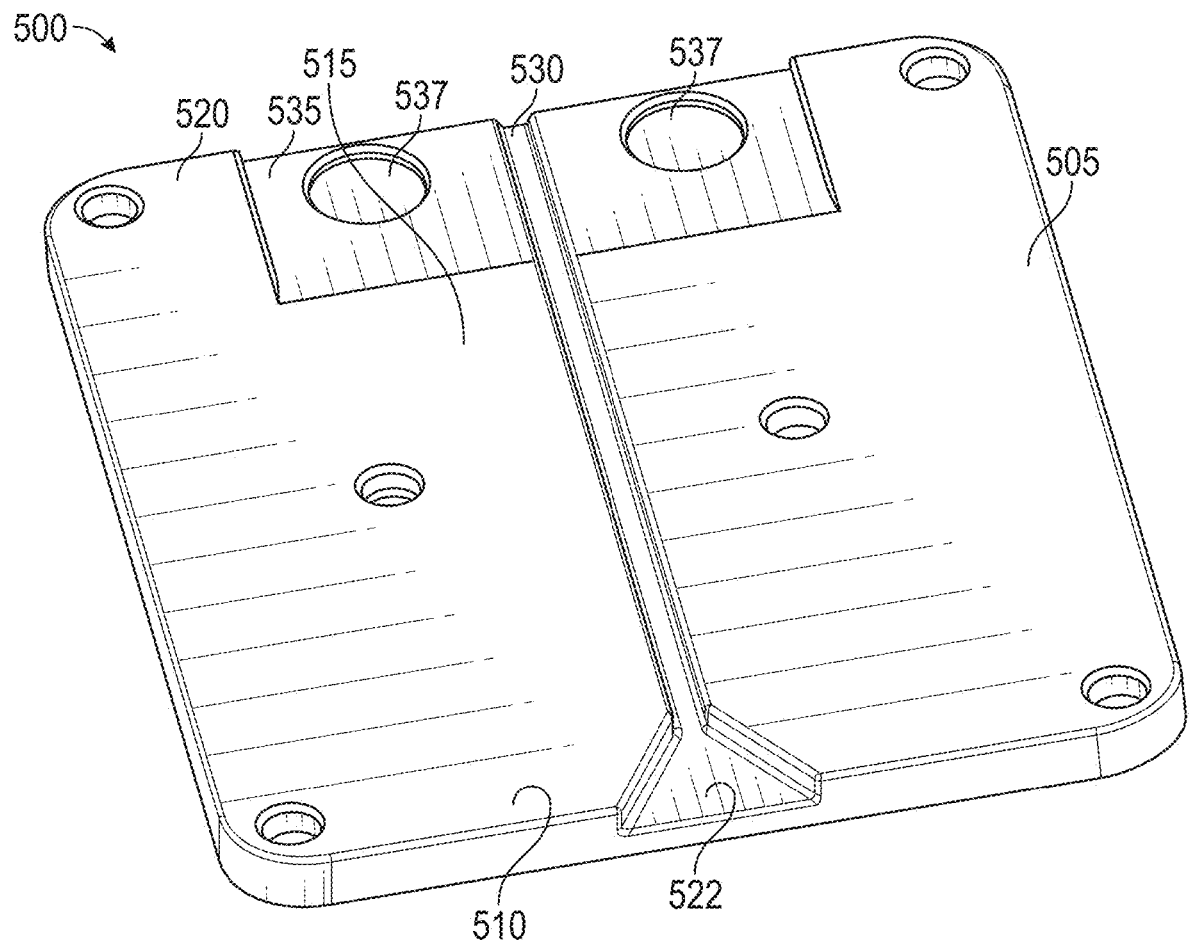
FIG. 14 is a perspective view of a package described in at least one embodiment herein.

In FIG. 14, the package 500 includes a base 505 having an area 515 configured to receive an implantable sheet. The base 505 further includes a first channel 530 formed in the base 505 below the area 515 configured to receive the implantable sheet. The first channel 530 is centered beneath the area 515 configured to receive the sheet. Although not shown in FIG. 14, the area 515 configured for receiving the sheet can be defined with a sheet recess defined within the base 505.

The first channel 530 is configured to receive any of the various delivery tools described herein. In some embodiments, the first channel 530 is approximately the same width as the delivery tool thereby allowing the delivery tool to frictionally fit within the first channel 530. In some embodiments, the first channel 530 may be wider than the delivery tool and may be designed to store both the delivery tool and the insertion member side-by-side. The first channel 530 also widens on the proximal end portion 510 of the base 505 to form a mouth 522. In some embodiments, the mouth 522 is generally triangular.

On the distal end portion 520 of the base 505, the first channel 530 passes through a recess 535 including one or more finger engagement recesses 537. The one or more finger engagement recesses 537 being further defined within the recess 535 and the base 505. The one or more finger engagement recesses 537 being positioned on either side of the first channel 530. The finger engagement recesses 537 are designed to allow the surgeon to push down into the implantable sheet and into the finger recesses 537 to provide the sheet at the proper angle for securing the sheet in the slot in the distal end portion of the delivery tool. The package depicted in FIG. 14 may be a blister pack designed to further include a cover.

Figure 15A:
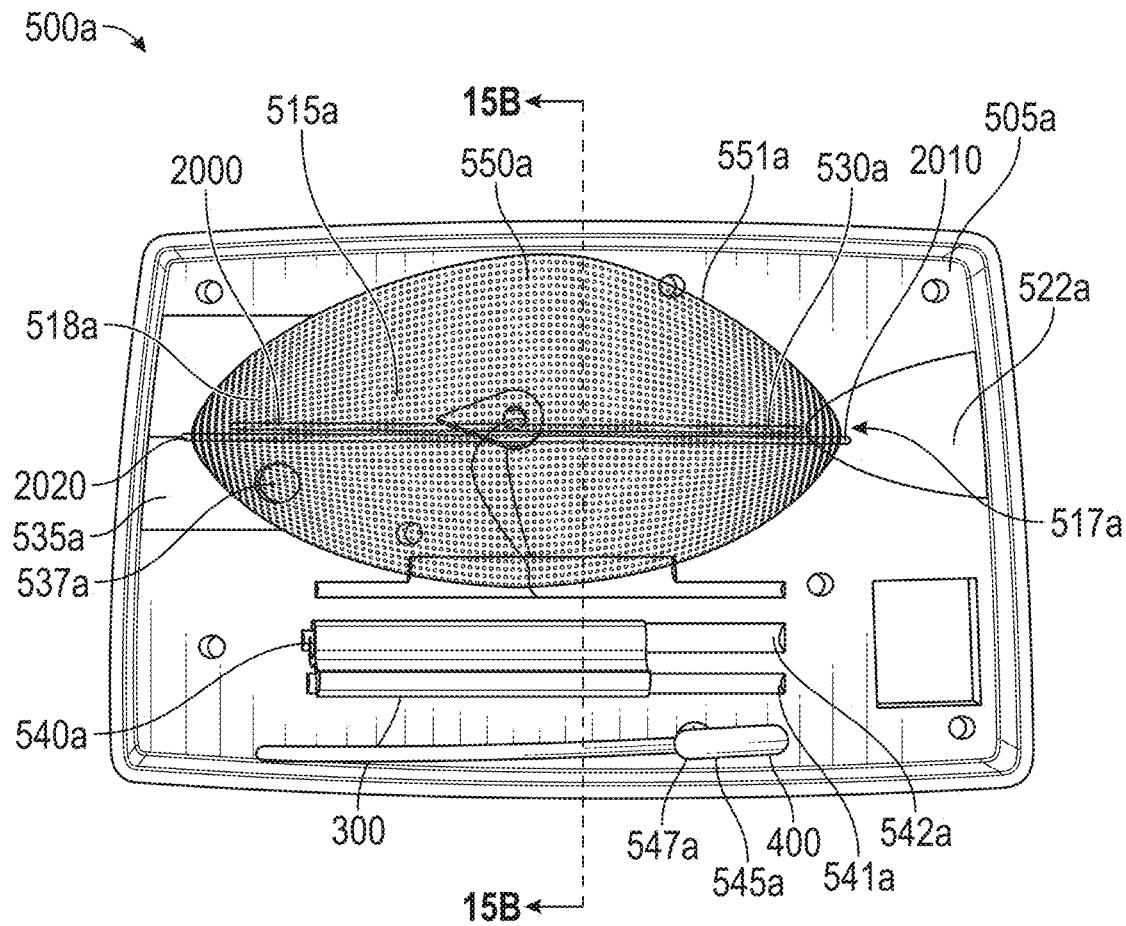
FIGS. 15A-15B include a top view and cross-sectional view of a package described in at least one embodiment herein.
Figure 15B:
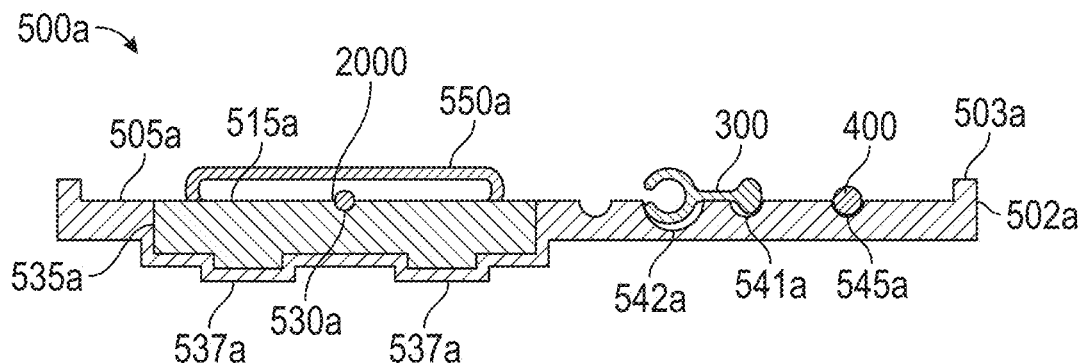

Another package 500a is shown in FIGS. 15A-15B, wherein the package 500a includes a base 505a having an area 515a configured to receive an implantable sheet 550a, such as a surgical mesh. The base 505a further includes a first channel 530a formed in the base 505a below the area 515a configured to receive the implantable sheet 550a. The first channel 530a being centered on a width of the sheet 550a and extending beyond an entire length of the sheet 550a. The delivery device 2000 is positioned within the first channel 530a. As shown, the proximal and distal end portions 2010, 2020 of the delivery tool 2000 extend beyond the outer edges 551a of the sheet 550a.

As illustrated, in some embodiments, the proximal end portion 517a of the first channel 530a widens to make it easier for the surgeon to handle the proximal end portion 2010 of the delivery tool 2000 without touching the outer edge 551a of the sheet 550a. In some embodiments, the proximal end portion 517a of the first channel 530a widens into a mouth 522a having a triangular shape with rounded edges. In some embodiments, the distal end portion 518a of the first channel 530a passes through a recess 535a having a generally square or rectangular shape. The recess 535a is wider than the first channel 530a. The recess 535a further includes one or more finger engagement recesses 537a formed deeper into the base 505a than the recess 535a.

As further illustrated in FIG. 15A, the base 505a of the package 500a further includes at least a second channel 540a formed therein and configured to receive and store any of the rolling devices 300 described herein and at least a third channel 545a formed therein and configured to receive and store any of the various insertion members 400 described herein. In some embodiments, the first, second and third channels 530a, 540a, 545a are parallel to each other in the base 505a. As depicted, in some embodiments, the second channel 540a includes a thin channel 541a and a thicker channel 542a spaced apart from each other by a small distance. The thin channel 541a is meant to receive at least a portion of the peak of the fin of the rolling device 300 and the thicker channel 542a is meant to receive at least a portion of the tubular body of the rolling device 300. The third channel 545a is configured to frictionally fit the insertion member 400 while the second channel(s) are not configured to frictionally fit the rolling device 300. The third channel 545a may include a side cut-out 547a to allow easier access to the handle of the insertion member 400.

As specifically shown in FIG. 15B, the package 500a is surrounded on the perimeter by an outer wall 502a which is connected to a top edge 503a extending therefrom around the entire perimeter of the package 500. Although not shown, it is envisioned that the cover of the package 500a may be applied or sealed to the top edge 503a. In addition, as further illustrated, the base 505a is inclined slightly to allow the sheet 550a to be put into a better position for being secured to the delivery tool.

In some embodiments, as shown in FIG. 15A, the implantable sheet is pre-loaded into the slot of the distal end portion of the delivery tool. In such embodiments, the delivery tool and the implantable sheet are in direct contact with each other within the package and/or while the delivery tool is within the first channel.

As depicted in FIG. 16, in some embodiments, the package 500b, shown in cross-section, includes a base 505b having an inclined surface in the area 515b where the implantable sheet 550b is received and stored. The incline surface tips and maintains the sheet 550b at an angle making it easier to assemble the components together, and particularly, when securing the sheet 550b to the delivery tool 200.

Also shown in FIG. 16, the first channel 530b formed in the base 505b of the package 500b may be a gutter 560b configured to keep the delivery tool 200 and the sheet 550b separate from each other and/or unable to make direct contact with each other while maintained in their respective locations within the package 500b. The gutter still includes a top portion which is open to the top surface of the base, however the gutter 560b extends away from the base 505b a sufficient amount to vertically space the delivery tool 200 and the sheet 550b inside the package 500b. The gutter 560b may surround a majority of the delivery tool to prevent direct contact between the sheet 550b and the delivery tool 200. However, the gutter 560b will remain sufficiently open to enable extraction of the delivery tool therefrom.

Although spaced from each other physically, the delivery tool 200 and the sheet 550b are connected to each other indirectly via a central tie 570b. The central tie 570b is secured to a central portion or center of the sheet 550b and extends away from the sheet surface in the form of a loop 571. Inside the package, the loop 571 extends from the sheet 550b through the top portion of the gutter 560b or channel 530b and is positioned within the gutter 560b or channel 530b with the delivery tool 200 positioned within the loop 571. The delivery tool 200 being directly connected to the suture loop 571 and indirectly connected to the sheet 550b.

The base 505b of FIG. 16, further includes a first and second leg 580b (in cross-section) formed into the base and extending away from the top surface of the base 505b. The first and second legs 580b are configured to stabilize the base 505b on a flat surface by keeping the gutter 560b or channel 530b from touching a flat surface to stabilize the package 500b and prevent teetering. In some embodiments, the base includes two legs extending a length of the base to stabilize the base on a flat surface. In some embodiments, the base includes three or more legs independently and strategically positioned on the base in a manner which stabilizes the base on a flat surface.

The base described herein can be made of any suitable sterilizable material. Some non-limiting examples include, but are not limited to, polyvinylchloride (PVC), polyethylene terephthalate (PET), or polyethylene terephthalate glycol (PETG), polypropylene, polyethylene. In some embodiments, the package is a molded, preformed blister package including a base as described herein. The package may further include a cover (not shown). The cover may be a peelable cover made of a heat-sealable plastic material or foil. Alternatively, the cover may be made of the same sterilizable material as the base and can be friction fit to the base and if need sealed within an outer package for sterility purposes.

VII. Sheet-Tool Assembly

In FIG. 17A-17C, a sheet-tool assembly 600 is depicted wherein the implantable sheet 650 is shown secured to the delivery tool 200 by a central tie 660 wherein the loop 670 of the central tie 660 extends from a bottom side 651 of the sheet 650 and surrounds a portion of the delivery tool 200. The tie handles 675 are positioned on a top side 652 of the sheet 650 opposite the bottom side 651. In some embodiments, the implantable sheet is a surgical mesh and the sheet-tool assembly is a mesh-tool assembly.

In some embodiments, a portion of the sheet 650, and particularly a distal edge portion 653 of the sheet 650, may be secured within the slot 231 defined within a distal end portion 220 of the delivery device 200 in the sheet-tool assembly 600. In some embodiments, only a distal edge portion 653 of the sheet 650 is secured within the slot 231 defined within a distal end portion 220 of the delivery device 200 and a proximal edge portion 654 of the sheet 650 is free of the slot 231 in the sheet-tool assembly 600.

The sheet-tool assembly may be preassembled within the package or may be post-assembled after the package is opened and the components accessed.

VIII. Methods of Use

The present disclosure also provides methods of treating or repairing soft tissue defects with the use of the various components of the kits described herein. The kits and components described herein are intended to be used in any variety of surgical procedures wherein a soft tissue defect needs repair. In some embodiments, the kits and components described herein may be used to repair various types of hernia repair using TAPPS (transabdominal preperitoneal surgery). TEPS (totally extraperitoneal surgery) or IPOM (intra peritoneal onlay mesh) techniques. In some embodiments, the kits and components described herein may be used for ventral hernia repair using an IPOM (i.e. intraperitoneal) or a preperitoneal mesh placement. Any methods described herein directed to repairing a soft tissue defect or hernia is intended to be applicable specifically to ventral hernia repair and/or ventral hernia repair using an IPOM technique.

As provided in FIGS. 18A-19E, methods for repairing a soft tissue defect, such as a hernia or ventral hernia, may include the steps of preparing a sheet-tool assembly, preparing the sheet-tool assembly for insertion into the patient, inserting the sheet-tool assembly into the patient, orienting the sheet, deploying the sheet, positioning and fixating the implantable sheet, detaching the sheet from the delivery tool and central tie, and removing the central tie and the delivery tool from the patient.

Prior to using the components and/or kits described herein to treat or repair a soft tissue defect, at least some of the components may be combined or assembled. For example, in some embodiments, the implantable sheet, the central tie, and the delivery tool may be assembled to form a sheet-tool assembly, wherein the central tie, the delivery tool, and the implantable sheet are combined in one or more additional procedural steps. For example, in some embodiments, a method of forming a sheet-tool assembly is described and includes the steps of: providing an implantable sheet, such as a surgical mesh, having an outer edge defining a central portion; adding a central tie to the central portion of the sheet, such that a first portion of the central tie extends from a first bottom side of the implantable sheet forming a loop and a second portion of the central tie extends from a second top side, opposite the first bottom side, forming a tie handle; and positioning an elongate body of a delivery tool through the loop of the central tie thereby connecting the sheet to the delivery tool via the central tie to form a sheet-tool assembly. In some embodiments, an additional step of securing a portion of the outer edge of the sheet within a horizontal slot defined within a distal end portion of the delivery tool may also be performed to form the sheet-tool assembly.

In some embodiments, an implantable sheet, a central tie, and a delivery tool may be assembled after the package is opened. In other embodiments, an implantable sheet, a central tie, and a delivery tool may be pre-assembled inside the package.

In some embodiments, a surgical mesh, a central tie, and a delivery tool may be assembled to form a mesh-tool assembly after the package is opened. In other embodiments, a surgical mesh, a central tie, and a delivery tool may be pre-assembled to form a mesh-tool assembly inside the package.

Pre-assembly of the sheet with the delivery tool and the central tie provides the benefit of decreasing the length of time needed to perform the surgical procedure. Pre-assembly is also the easiest way for the medical personnel to handle the sheet and delivery tool prior to implantation. However, pre-assembly may add stress to the sheet, via the delivery tool, during storage or transportation which may lead to damage of the sheet, especially when the sheet includes a coating or the sheet is a composite mesh including additional layers such as an anti-adhesion barrier. Coatings and anti-adhesion barriers can be fragile and could suffer damage, such as cracks, scratches, chipping, etc. by rubbing against the delivery tool during shipment or storage.

In embodiments wherein the delivery tool described herein is designed to transform from a unidirectional tool to a multidirectional tool, two additional end ties can be positioned on the sheet outside the central portion of the sheet and near the outer edges of the sheet. The additional first and second end ties being positioned on opposite ends of the sheet with the central tie positioned therebetween. The end ties, like the central tie, each include a tie loop extending from a bottom side of the sheet and a tie handle positioned on an opposite top side of the sheet. When assembled, the proximal and distal end portions of the transformable multidirectional delivery tool will pass through the tie loops of the first and second end ties with the elongate body passing through the tie loop of the central tie. In some embodiments, the tie loops of the end ties may be positioned within the apertures configured to receive a suture on the proximal and/or distal end of the delivery tool.

Figure 18A:
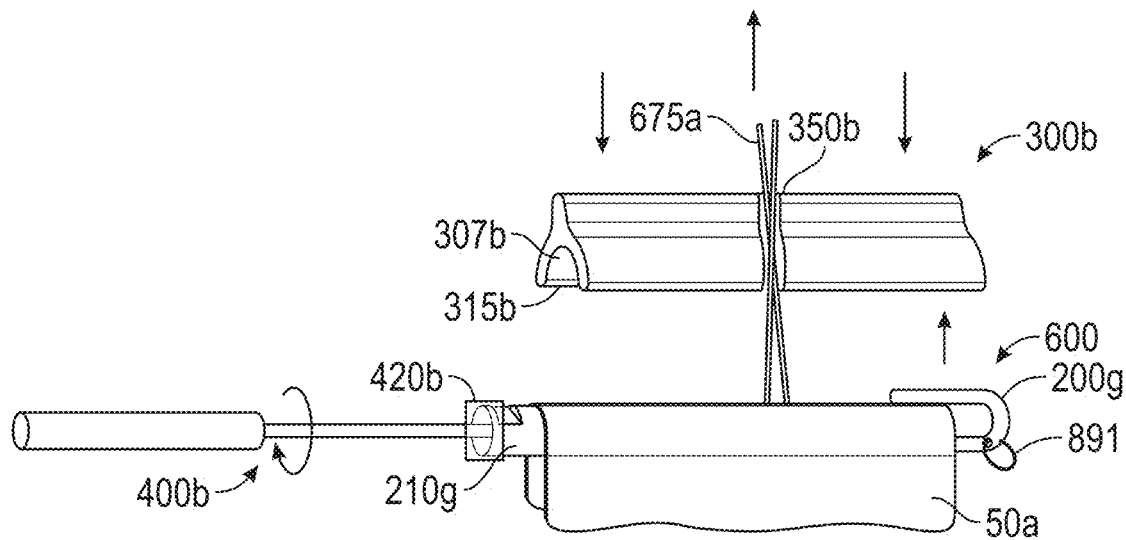
FIGS. 18A-18B include a side view of a rolled mesh-tool assembly described in at least one embodiment herein.
Figure 18B:
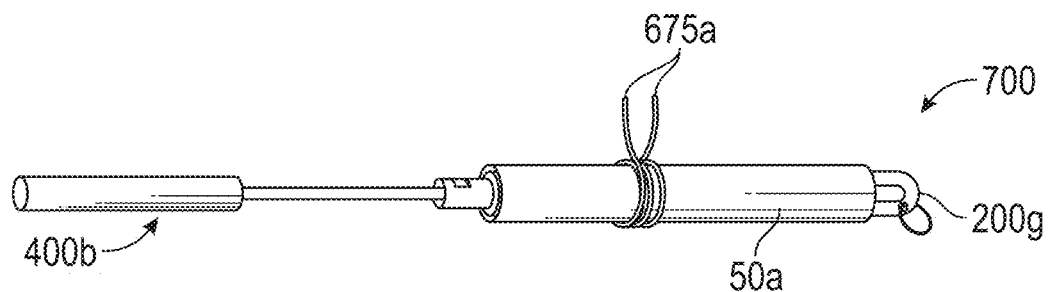
Figure 19A:
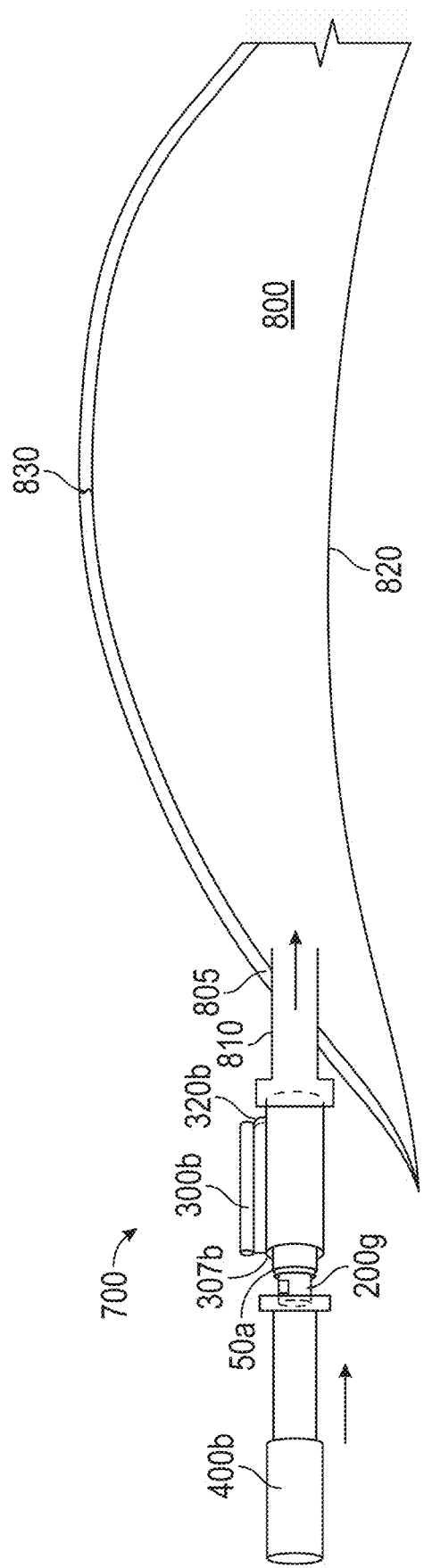
Figure 19B:
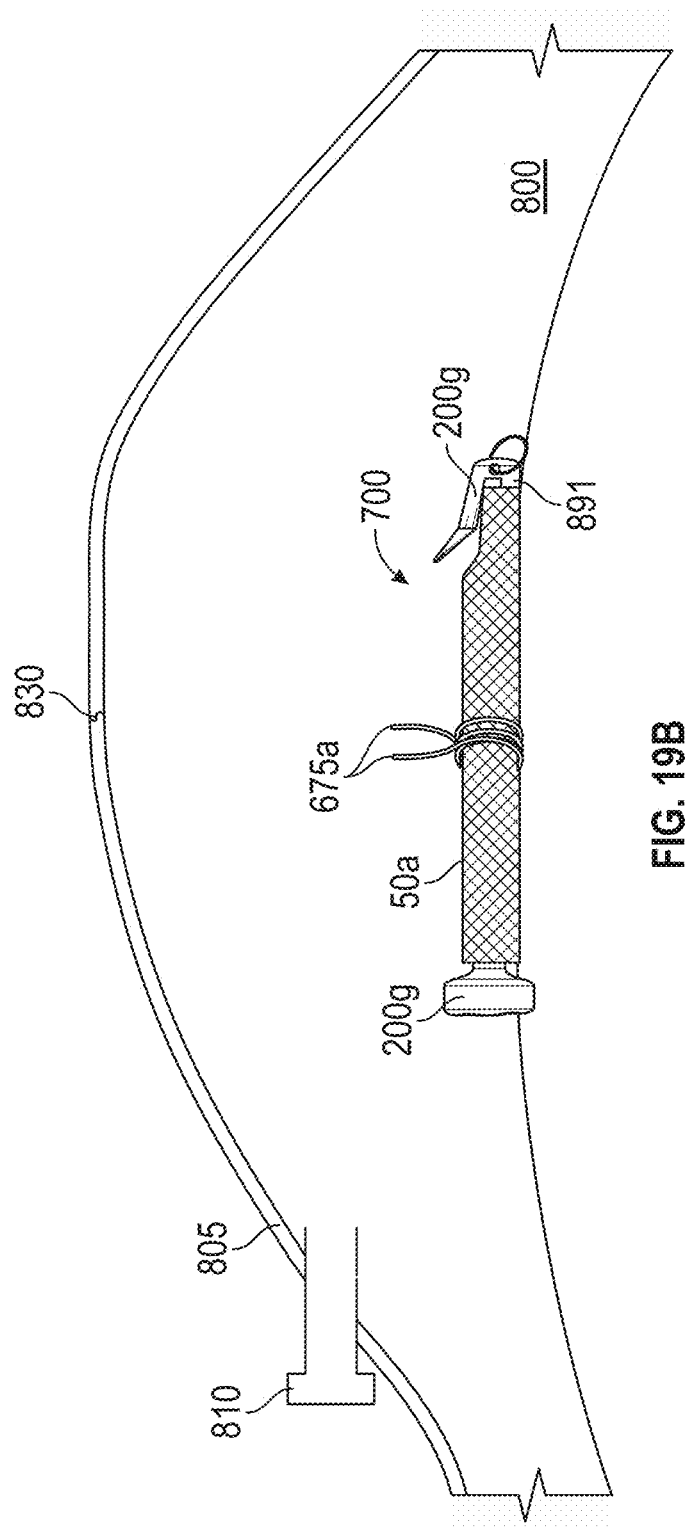
Figure 19C:
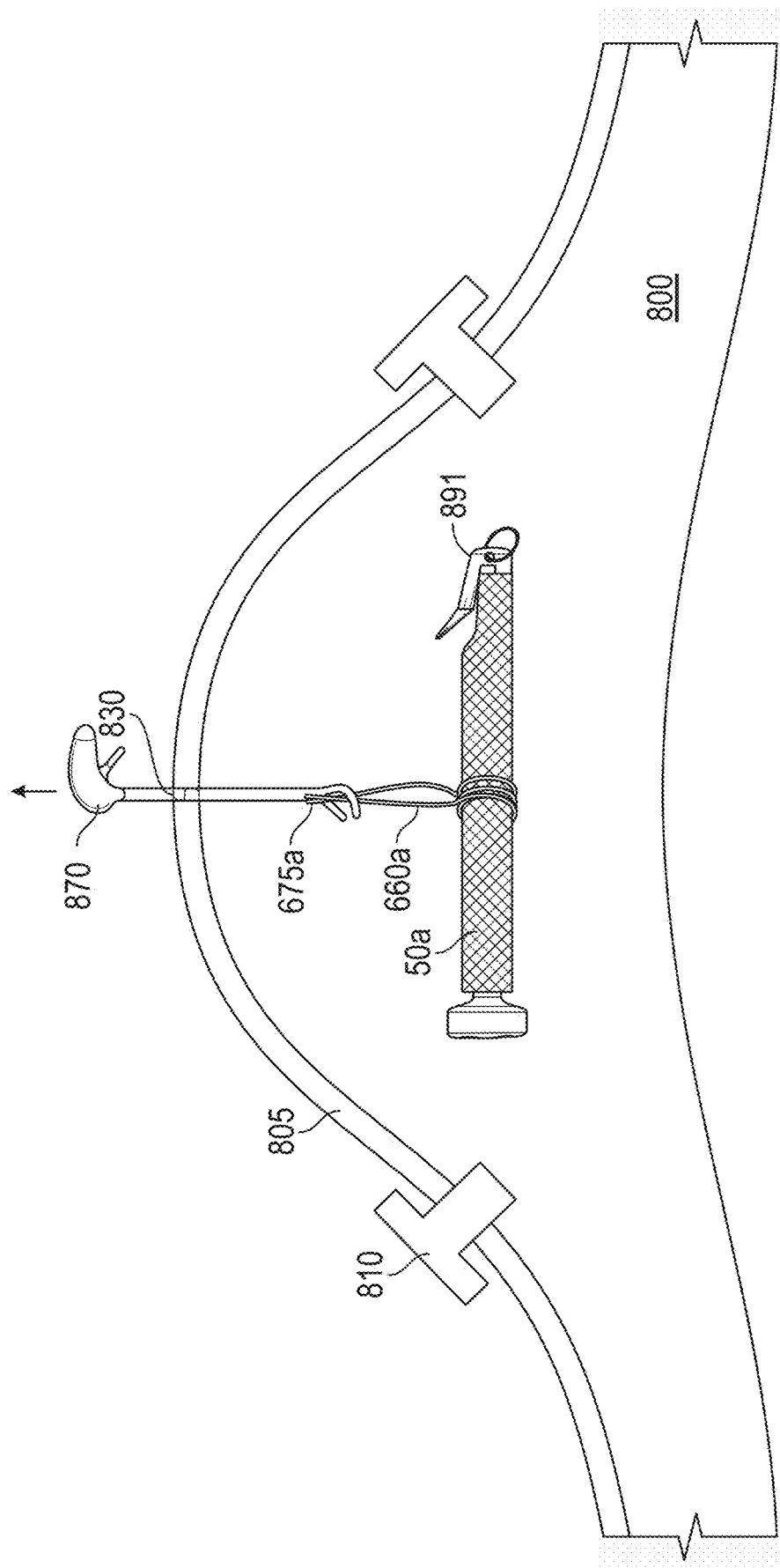
Figure 19D:
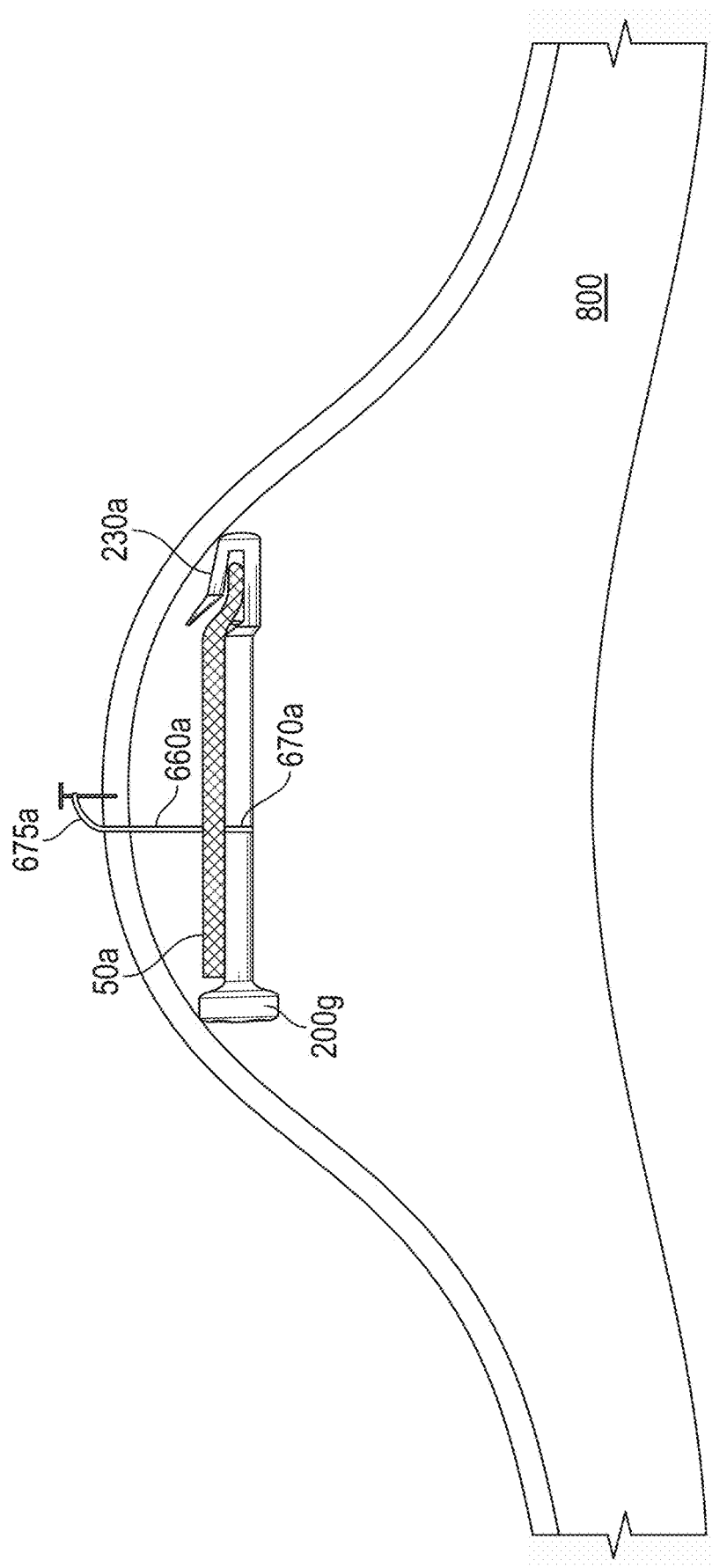

Once assembled, the implantable sheet, the central tie, and the delivery tool, i.e., the sheet-tool assembly, can be prepared for insertion into the patient. For example, as shown in FIGS. 18A-18B, in some embodiments, the sheet-tool assembly 600, whether pre-assembled within the package or post-assembled after the package is opened, can be combined with a rolling device 300b and an insertion member 400b to roll the sheet 50a around the exterior of the delivery tool 200g in one or more additional procedural steps. In some embodiments, a method of preparing a rolled sheet-tool assembly 700, such as a rolled mesh-tool assembly, for insertion into a patient is described and includes the steps of: passing the tie handle 675a positioned on a top side of the sheet 50a through a handle opening 350b defined in at least a portion of the rolling device 300b; pulling upon the tie handle 675a (as indicated by the arrow above the handle) until the sheet-tool assembly 600 is positioned within a channel 307b defined within the rolling device 300b; and rotating the delivery tool 200g within the channel 307b of the rolling device 300b causing the sheet 50a to roll onto itself around the outer surface of the delivery tool 200g to form a rolled implantable sheet or a rolled sheet-tool assembly 700 within the rolling device 300b. In some embodiments, a distal end portion 420b of an insertion member 400b, and particularly a socket on the distal end portion 420b of the insertion member 400b, can be secured to the shaped proximal end 210g of the delivery tool 200g prior to rolling. In such embodiments, the step of rotating the delivery tool 200g can be performed by rotating the insertion member 400b attached thereto (as indicated by the arrow positioned on the insertion member 400b). By using the insertion member, contact to the proximal end of the delivery tool is avoided to reduce the likelihood of contamination.

Once the sheet is prepared in a rolled configuration or the rolled sheet-tool assembly 700 is prepared, the rolled sheet or rolled sheet-tool assembly 700 can be inserted into an abdominal cavity of a patient. For example, as shown in FIGS. 19A-19E, in some embodiments, a method of inserting a rolled sheet or rolled sheet-tool assembly is described and includes the steps of: attaching a distal end 320b of the rolling device 300b to a trocar 810 extending from the patient's body 805, such as the abdomen; and moving or pushing the insertion member 400b in a distal direction through the channel 307b of the rolling device 300b and into the trocar 810 until the delivery tool 200g including the sheet 50a in a rolled configuration or the rolled sheet-tool assembly 700 completely enters a cavity 800 within the patient, such as the abdominal cavity 800. In some embodiments, the rolling device 300b and the insertion member 400b can be used as handles during the insertion process to carry the rolled sheet 50a and tool 200g from the package to the trocar 810. A surgeon can easily grab the rolling device 300b on one end and the insertion member 400b on an opposite end, with the sheet 50a and delivery tool 200g positioned therebetween in a rolled configuration, to perform inserting the sheet 50a and delivery tool 200g into the patient. Since the rolling device 300b and the insertion member 400b are not intended to enter the patient contact does not need to be avoided. This design also prevents or limits the amount of direct contact with the implantable sheet and the delivery tool thereby reducing the likelihood of contamination.

Following insertion, the rolled sheet or the rolled sheet-tool assembly 700 is free of both the rolling device 300b and the insertion member 400b. However, the sheet or sheet-tool assembly 700 is still in a rolled configuration and needs to be deployed within the cavity of the patient. For example, as sown in FIGS. 19C-19D, in some embodiments, a method of deploying the rolled implantable sheet or rolled sheet-tool assembly is described and includes the steps of: introducing a suture catcher 870, such as an Endoclose™, into the patient or body cavity 800 by penetrating through a center of the soft tissue defect or hernia 830 from outside the patient or body cavity; grasping the tie handle 675a of the central tie 660a extending from the rolled sheet configuration 700, pulling the tie handle 675a back through the tissue defect or hernia 830 to the outside of the patient thereby releasing the rolled sheet 50a of constraint by the tie handle 675a; and securing the tie handle 675a outside the patient 800. The tie handle can be secured outside the patient with any type of fastener. Because the delivery tool 200g is still attached to the sheet 50a through the tie loop 670a of the central tie 660a, the pulling of the tie handle 675a out through the tissue defect or hernia 830, causes the tie loop 670a to force the delivery tool 200g against the underside of the tissue defect or hernia 830 with the sheet 50a positioned therebetween. The combination of the central tie 660a and the delivery tool 200g lifts and holds the sheet 50a up against the underside of the tissue defect. The rolled sheet unrolls automatically and deploys inside the patient or the abdominal cavity. During deployment or the method of deploying the sheet, the outer edge of the sheet 50a remains secured within the slot 230g of the delivery tool 200g. In addition, by passing the suture catcher 870 through the center of the defect 830, the final placement of the sheet 50a is likely to also be centered on the defect 830.

In some embodiments wherein the delivery tool is transformable to a multidirectional tool, the methods of deployment may further include the steps of: introducing a suture catcher, such as an Endoclose™, into the patient or body cavity by penetrating through an outer perimeter of the hernia defect from outside the patient or body cavity; grasping the tie handle of the first end tie extending from the sheet, pulling the tie handle of the first end tie back through the tissue to the outside of the patient; and securing the tie handle of the first end tie outside the patient. This same process can be repeated only the catcher grabs the tie handle of the second end tie from an outer perimeter of the hernia defect positioned on an opposite end of the defect with the central tie positioned therebetween and aligned with the central tie and the first end tie. Once the first and second end ties are secured outside the body, the sheet and delivery tool will be securely suspended below the defect and the central tie can be cut or removed to allow the delivery tool to transition from a generally unidirectional tool to a multidirectional tool thereby enhancing the ability of the delivery tool to deploy the implantable sheet more completely. As provided hereinabove, the transition may be performed manually, naturally, or via spring-loaded system.

Following orientation, the deployment, final placement and/or positioning of the implantable sheet, such as a surgical mesh, can be determined and the sheet can be fixated in or around the tissue defect or hernia. For example, in some embodiments, a method of placing and fixating the suspended sheet is described and includes the steps of: manipulating the suspended sheet with a laparoscopic surgical grasper into a final position; and fixating the sheet into tissue in or around the tissue defect while the delivery tool and the central tie maintain the sheet up against the underside of the defect. Any standard laparoscopic surgical grasper or standard surgical fastening device, such as a tack or clip applier, stapler, or suturing device, may be introduced into the patient or a cavity within a patient, such as the abdominal cavity, via one or more trocars. Because the sheet remains suspended up against the defect while being positioned and/or fixated, both hands of the surgeon are free to work in unison to position and fixate the sheet to the tissue. The sheet can be fixated using any suitable fixation means, including, but not intended to be limited to, sutures, clips, tacks, staples, adhesives, and the like. During positioning and/or fixating of the sheet, the outer edge of the sheet remains secured within the slot of the delivery tool.

Following fixation of the sheet, the delivery tool 200g and the central tie 660a, including tie handle 675a, can be separated from the sheet 50a and withdrawn from the patient's body 800. For example, as shown in FIG. 19E, in some embodiments, a method of withdrawing the delivery tool and central tie from the site of implantation is described and includes the steps of: freeing the sheet 50a, and particularly the outer edge of the sheet, from the slot 230g defined within the distal end portion of the delivery tool 200g; cutting the tie handle 675a secured outside the patient, thus freeing the central tie 660a from both the delivery tool 200g and the sheet 50a; and withdrawing the delivery tool 200g and central tie 660a from inside the patient. In some embodiments, the laparoscopic surgical grasper 890 can be utilized to free the slot 230g in the distal end portion of the delivery tool 200g from the sheet 50a. The grasper 890 can be used to grab the distal end of the delivery tool 200g, and particularly a looped suture 891 positioned through the suture aperture on the distal end portion of the delivery tool 200g, to slide the distal end portion of delivery tool 200g away from the outer edge of the sheet 50a thereby removing the sheet 50a from the delivery tool 200g. The looped suture can be added to the delivery tool during manufacturing of the delivery tool or immediately prior to insertion by the surgeon. In addition, the tie handle extending outside the patient can be cut or unfastened and pulled from outside the patient, making the delivery tool 200g detach from the central portion of the sheet 50a and fall down into the bottom of the abdominal cavity 800. The delivery tool 200g can then be withdrawn or retrieved from inside the patient by using the grasper 890 to grab the looped suture 891 on the distal end of the tool 200g and withdrawing the tool 200g back through the trocar 810 and out of the patient. Because the delivery tool is flexible, the delivery tool does not need to be perfectly aligned with the trocar to be removed. In the event, any portion of the central tie which remains inside the cavity after cutting, the grasper may also be used to withdraw the central tie.

In some embodiments wherein end ties are utilized as well, the end ties can also be cut and/or removed from both the sheet and the delivery tool after the sheet is positioned and fixated, similar to the central tie.

In some embodiments wherein the delivery tool transitions into a multidirectional tool, withdrawing of the multidirectional tool may further require the step of transitioning the tool back to a unidirectional tool prior to withdrawal, to be able to pass back through the trocar upon exiting the cavity. In some embodiments, the transition can be performed manually by a surgeon, using either standard laparoscopic or robotic instruments. In some embodiments, the surgeon will have to grab the correct end of the tool which allows the wall of the trocar to force the arms, which have a natural bias to extend away from the elongate body, back towards the elongate body so the delivery tool can be passed through the trocar. For example, the multidirectional tool in FIG. 7E includes arms which have a natural bias to extend away from the elongate body from a common point near the distal end portion of the tool. To remove the tool of FIG. 7E, the surgeon could grab the distal end portion of the tool and pull it into and through the trocar. As the tool is moved through the trocar in a distal direction, the walls of the trocar will overcome the natural bias of the arms forcing them back towards the elongate body for easy withdrawal. In the event the surgeon grabbed the proximal end of the tool of FIG. 7E, the arms would not move back towards the elongate body, but rather be forced farther apart by the walls of the trocar and therefore unable to be removed with breaking.

In some embodiments, methods of repairing or treating a hernia repair includes the steps of: providing an implantable sheet having a central tie extending therefrom, the central tie including a tie loop extending from a first bottom side of the sheet and at least one tie handle positioned on a second top side of the sheet opposite the first side; positioning an elongate body of a sheet delivery tool within the tie loop of the central tie, the elongate body extending between a proximal end portion and a distal end portion of the sheet delivery tool; inserting a portion of an outer edge of the implantable sheet into a horizontal slot defined in the distal end portion of the sheet delivery tool to secure the sheet within the slot of the delivery tool; passing the at least one tie handle through a suture opening in a sheet rolling device; pulling the at least one tie handle until the sheet and flexible sheet delivery tool are pulled into a channel of the sheet rolling device, attaching an insertion member to a proximal end portion of the sheet delivery tool; rotating the insertion member causing the sheet to roll onto itself around the sheet delivery tool and within the channel of the sheet rolling device to form a rolled implantable sheet and/or a rolled sheet-tool assembly; inserting the rolled implantable sheet and delivery tool through a trocar and into the abdominal cavity of a patient; introducing a surgical grasper through a center of the hernia defect to grab the tie handle; pulling the grasper and tie handle back out of the patient through the center of the hernia defect deploying the sheet and causing the tie loop of the central tie and the delivery tool to suspend from a top of the cavity with the sheet positioned therebetween; positioning and fixating the sheet to the tissue in or around the hernia defect; freeing the sheet and the central tie from the sheet; and withdrawing the delivery tool, and possibly the central tie, from the abdominal cavity or patient.

In some embodiments, methods of repairing or treating a hernia repair includes the steps of: inserting a sheet in a rolled configuration into a cavity of a patient, the sheet rolled around an outer surface of a delivery tool and including an outer edge portion of the sheet secured within a slot defined in a distal end portion of the delivery tool, and an elongate body of the delivery tool connected to the sheet via a tie loop of a central tie extending from a bottom side of the sheet, the central tie further including a tie handle positioned on a top side of the sheet opposite the bottom side; withdrawing the tie handle through a center of the hernia defect from inside the cavity to the outside of the patient thereby suspending the sheet and the delivery tool via the central tie from a top surface of the abdominal cavity; deploying of the sheet into an unrolled configuration; positioning and fixating the sheet in or around the hernia defect; freeing the central tie and delivery tool from the sheet; and withdrawing the delivery tool, and possibly the central tie, from the abdominal cavity or patient.

In some embodiments, methods of repairing or treating a hernia repair includes the steps of: providing an implantable mesh having a central tie extending therefrom, the central tie including a tie loop extending from a first bottom side of the mesh and at least one tie handle positioned on a second top side of the mesh opposite the first side; positioning an elongate body of a mesh delivery tool within the tie loop of the central tie, the elongate body extending between a proximal end portion and a distal end portion of the mesh delivery tool; inserting a portion of an outer edge of the implantable mesh into a horizontal slot defined in the distal end portion of the mesh delivery tool to secure the mesh within the slot of the delivery tool; passing the at least one tie handle through a suture opening in a mesh rolling device, pulling the at least one tie handle until the mesh and flexible mesh delivery tool are pulled into a channel of the mesh rolling device; attaching an insertion member to a proximal end portion of the mesh delivery tool; rotating the insertion member causing the mesh to roll onto itself around the mesh delivery tool and within the channel of the mesh rolling device to form a rolled implantable mesh and/or a rolled mesh-tool assembly; inserting the rolled implantable mesh and delivery tool through a trocar and into the abdominal cavity of a patient; introducing a surgical grasper through a center of the hernia defect to grab the tie handle; pulling the grasper and tie handle back out of the patient through the center of the hernia defect deploying the mesh and causing the tie loop of the central tie and the delivery tool to suspend from a top of the cavity with the mesh positioned therebetween; positioning and fixating the mesh to the tissue in or around the hernia defect; freeing the mesh and the central tie from the mesh; and withdrawing the delivery tool, and possibly the central tie, from the abdominal cavity or patient.

In some embodiments, methods of repairing or treating a hernia repair includes the steps of: inserting a mesh in a rolled configuration into a cavity of a patient, the mesh rolled around an outer surface of a delivery tool and including an outer edge portion of the mesh secured within a slot defined in a distal end portion of the delivery tool, and an elongate body of the delivery tool connected to the mesh via a tie loop of a central tie extending from a bottom side of the mesh, the central tie further including a tie handle positioned on a top side of the mesh opposite the bottom side; withdrawing the tie handle through a center of the hernia defect from inside the cavity to the outside of the patient thereby suspending the mesh and the delivery tool via the central tie from a top surface of the abdominal cavity; deploying of the mesh into an unrolled configuration; positioning and fixating the mesh in or around the hernia defect; freeing the central tie and delivery tool from the mesh; and withdrawing the delivery tool, and possibly the central tie, from the abdominal cavity or patient.

It will be understood that various modifications may be made to the embodiments disclosed herein. Thus, those skilled in the art will envision other modifications within the scope and spirit of the disclosure.

EXAMPLES

Example 1

Figure 20A:
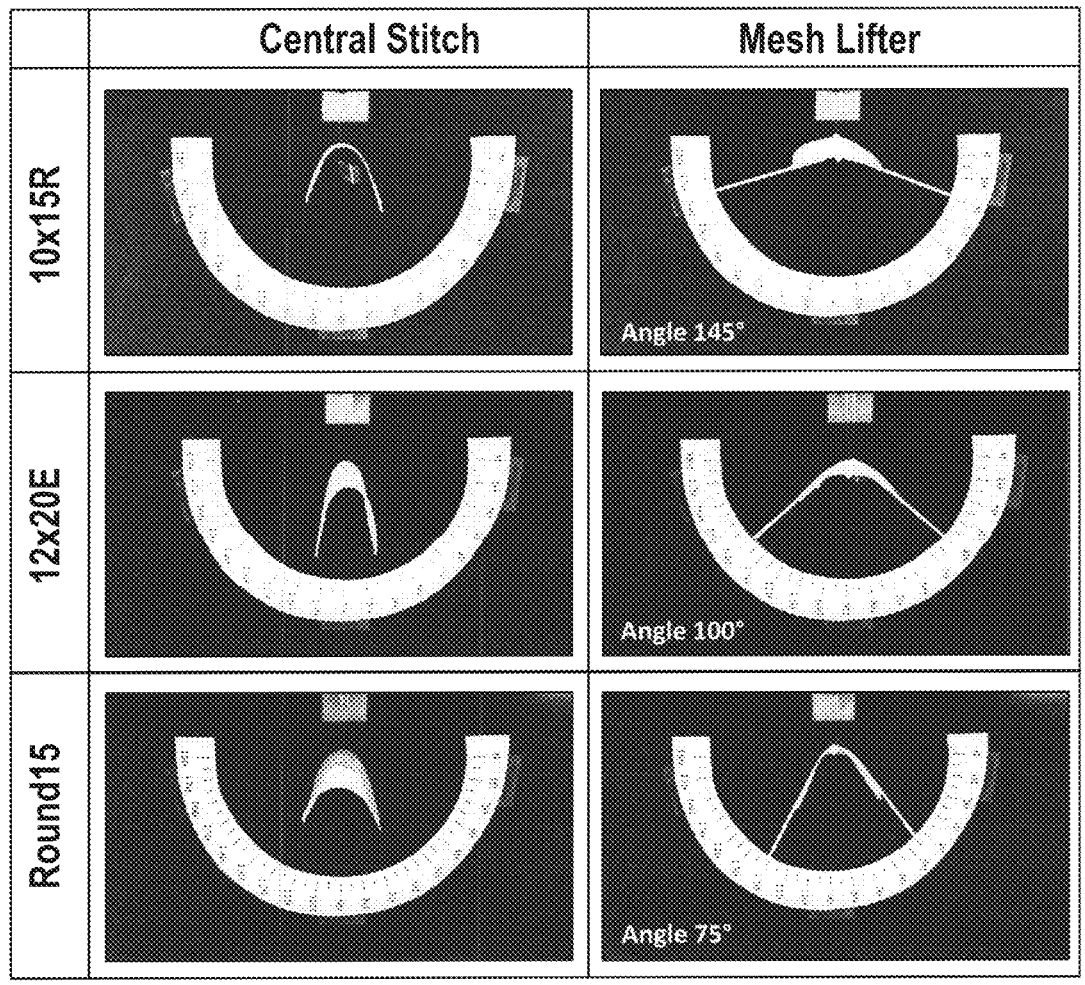
FIGS. 20A-22 are schematic images of testing results described in at least one of the examples provided herein.
Figure 20B:
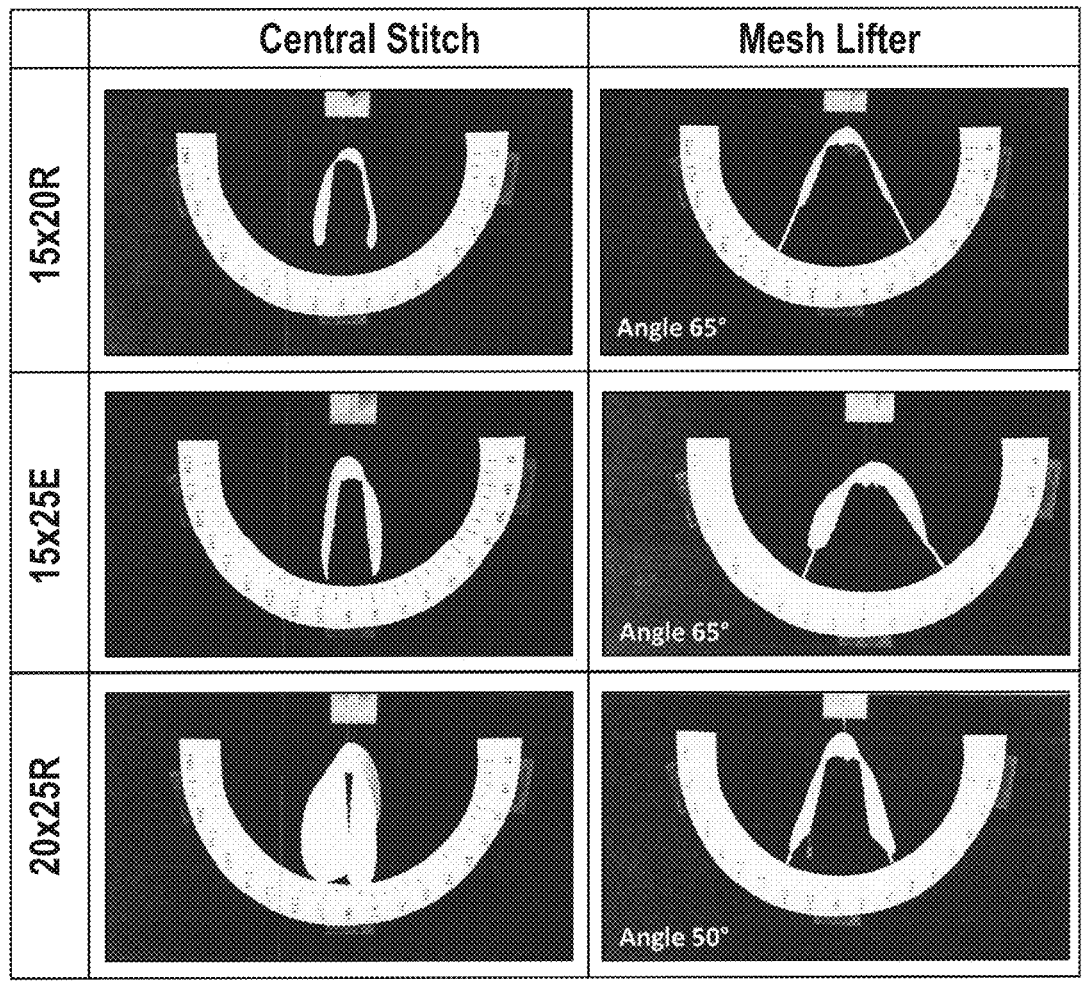

Several different sizes and shapes of the same implantable sheet (tested mesh: Symbotex™ ranging in size from 10×15 cms to 20×25 cms) were deployment tested. Each sheet tested was suspended from a central tie positioned on the center of the sheet, either alone or in combination with a unidirectional delivery tool as described herein. The deployment angle (DA) was measured for each, as well as the percent of volume. The results are summarized in Table 1 below. The results are also shown in FIGS. 20A-20B.

TABLE 1

| Mesh Size | DA Central Tie Alone | DA Central Tie w/Lifter | DA Difference | % Increase in DA | % of Volume |
|---|---|---|---|---|---|
| 10 × 15R | 45 | 145 | 100 | 222 | 36 |
| 12 × 20E | 30 | 100 | 70 | 233 | 60 |
| 15Round | 50 | 75 | 25 | 50 | 88 |
| 15 × 20R | 25 | 65 | 40 | 160 | 88 |
| 15 × 25E | 20 | 65 | 45 | 225 | 88 |
| 20 × 25R | 15 | 50 | 35 | 233 | 98 |

As shown in Table 1, the combination of a central tie with a unidirectional delivery tool as described herein provides a deployment angle of at least 50 degrees. In some embodiments, the deployment angle is at least 65 degrees. In some embodiments, the deployment angle can range from about 50 to about 180 degrees. In some embodiments, the deployment angle can range from about 60 to about 170 degrees. In still other embodiments, the deployment angle can range from about 65 to about 150 degrees.

As further shown in Table 1, the combination of a central tie with a unidirectional delivery tool as described herein improves the deployment angle of a sheet, such as a surgical mesh, as compared to using a central tie alone. In some embodiments, the percentage increase in deployment angle can range from about 50 to about 250%. In some embodiments, the percentage increase in deployment angle can range from about 75 to about 235%. In still other embodiments, the percentage increase in deployment angle can range from about 100 to about 200%.

Example 2

Figure 21:
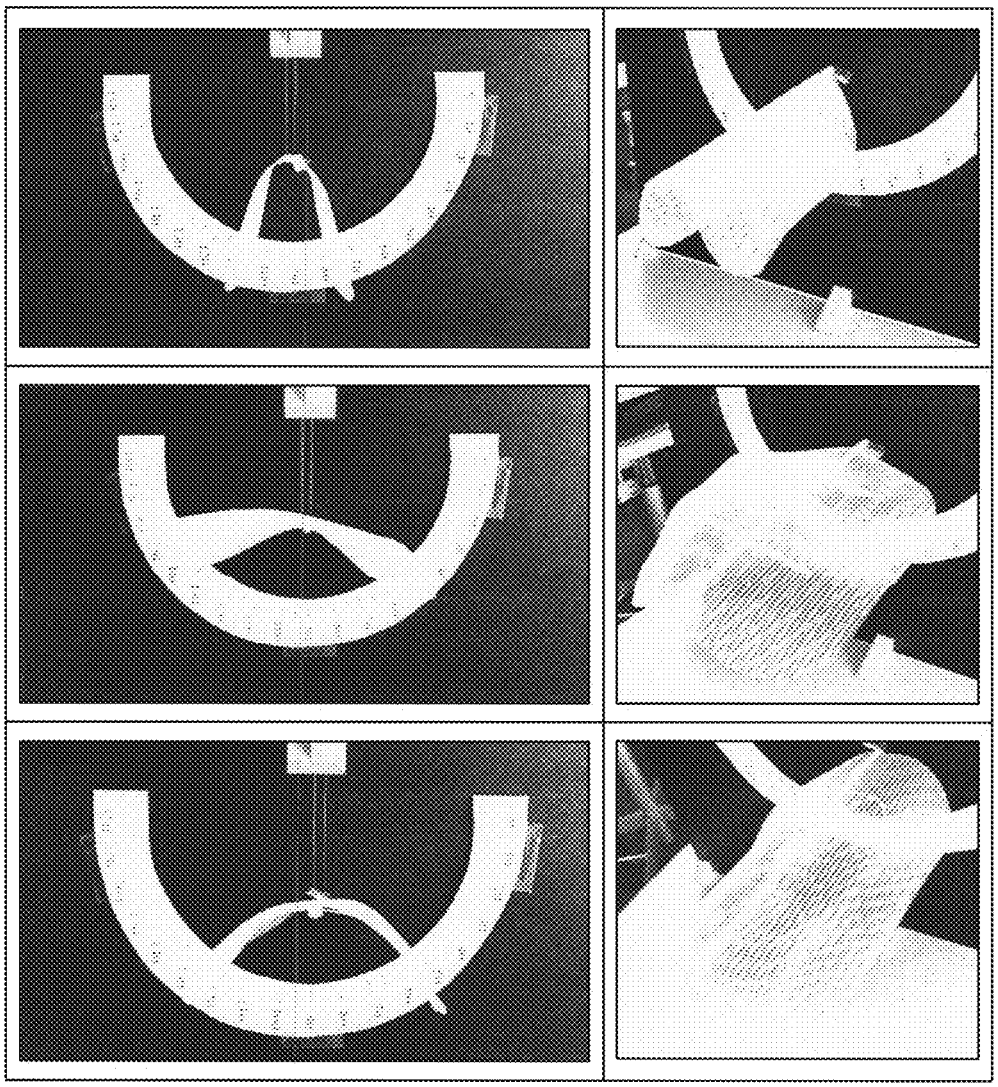

An implantable sheet (tested mesh: Symbotex™ 20×25 cm) was deployment tested using a unidirectional delivery tool as described herein or one of two different multidirectional delivery tools also described herein. The results are summarized in Table 2 below. The results are also shown in FIG. 21.

TABLE 2

| Delivery Tool | DA Central Tie w/Lifter | % Increase of DA over Single Axis |
|---|---|---|
| Single Axis | 30 | — |
| Multi-Axis Rotating Arms | 100 | 233 |
| Multi-Axis Resilient Arms | 70 | 133 |

Example 3

Figure 22:
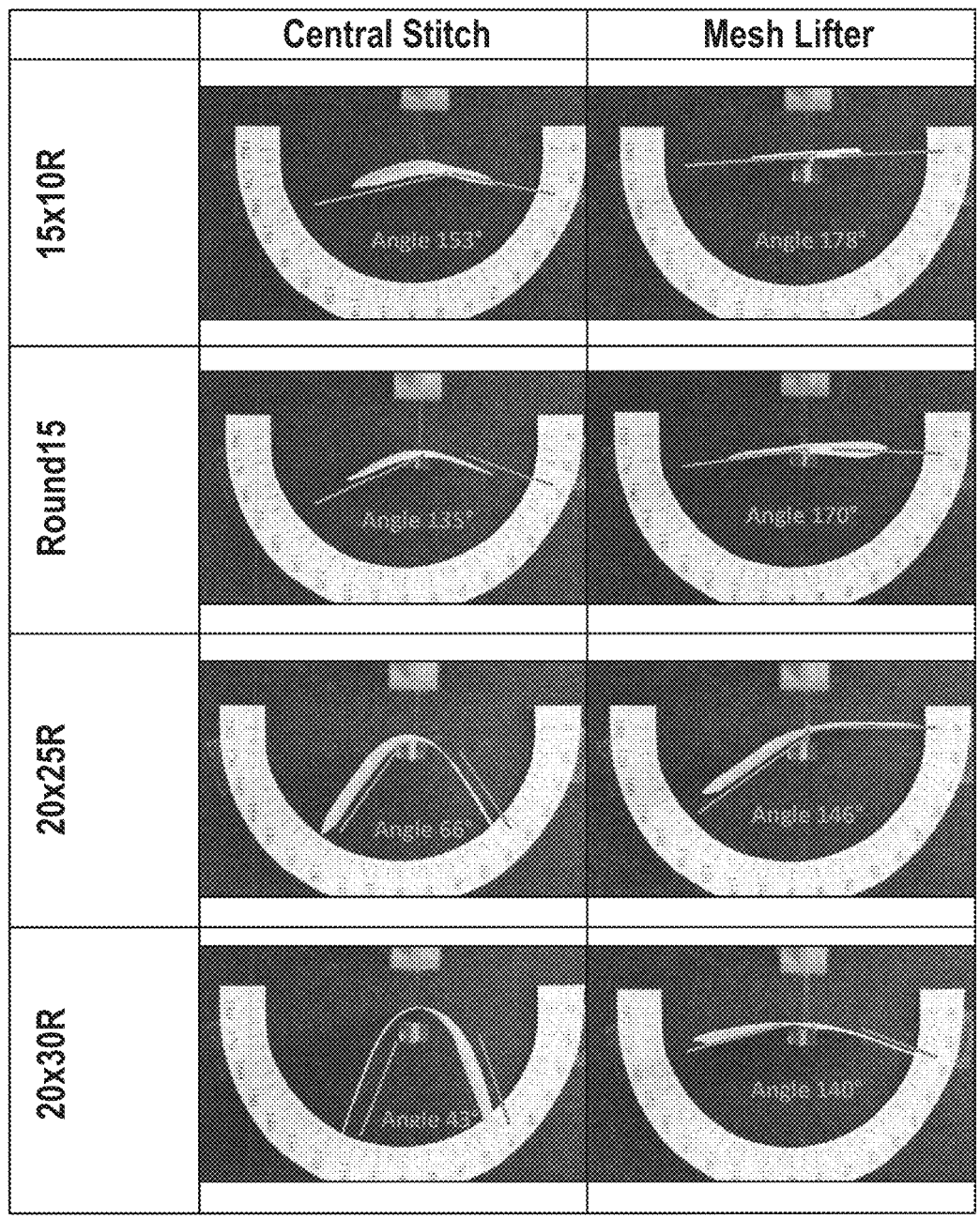

Several different sizes and shapes of the same implantable sheet (tested mesh: Parietene™ DS Composite Mesh ranging in size from 10×15 cms to 20×30 cms) were deployment tested. Each sheet tested was suspended from a central tie positioned on the center of the sheet, either alone or in combination with a unidirectional delivery tool as described herein. The deployment angle (DA) was measured for each, as well as the percent of volume. The results are summarized in Table 3 below. The results are also shown in FIG. 22.

TABLE 3

| Mesh Size | DA Central Tie Alone | DA Central Tie w/Lifter | DA Difference | % Increase in DA |
|---|---|---|---|---|
| 10 × 15R | 153 | 178 | 25 | 16 |
| 15Round | 135 | 170 | 35 | 26 |

TABLE 3-continued

| Mesh Size | DA Central Tie Alone | DA Central Tie w/Lifter | DA Difference | % Increase in DA |
|---|---|---|---|---|
| 20 × 25R | 66 | 146 | 80 | 121 |
| 20 × 30R | 43 | 140 | 97 | 225 |

The invention may also be described by the following numbered paragraphs:—

1. A surgical kit for hernia repair comprising:
an implantable sheet having a central tie passing therethrough, the central tie forming a tie loop extending from a bottom side of the implantable sheet and a tie handle positioned on a top side of the implantable sheet, and
a flexible delivery tool including an elongate body extending between a shaped proximal end portion and a distal end portion, the distal end portion including a clip attachment configured to secure a portion of the sheet within the distal end portion of the delivery tool.

2. The surgical kit of paragraph 1, wherein the implantable sheet and the delivery tool are preassembled to be indirectly connected to each other via the central tie, wherein the elongate body of the delivery tool passes through the tie loop of the central tie.

3. The surgical kit of paragraph 1, wherein at least a portion of an outer edge of the implantable sheet is secured within the clip attachment on the distal end portion of the flexible delivery tool.

4. The surgical kit of paragraph 1, wherein the clip attachment includes a slot extending longitudinally through the distal end portion of the flexible delivery tool, the slot positioned between an upper jaw member and a lower jaw member, wherein at least one of the upper and lower jaw members optionally includes at least one tooth or at least one recess configured to receive the tooth.

5. The surgical kit of paragraph 4, wherein the upper jaw member further includes a raised tension arm extending from the upper jaw member at a first angle and above an outer surface of the upper jaw member.

6. The surgical kit of paragraph 4, wherein the distal end portion of the flexible delivery tool further comprises a suture aperture defined therethrough and positioned distal to the slot of the attachment clip, the suture aperture configured to receive a looped suture suitable for grasping when withdrawing the flexible delivery tool from the patient.

7. The surgical kit of paragraph 1, wherein the distal end portion of the flexible delivery tool further comprises at least one crenulation extending outwardly from an outer surface of the distal end portion, the crenulation configured to engage openings in the implantable sheet when rolled.

8. The surgical kit of paragraph 1, further comprising a rolling device configured to roll the implantable sheet around the outer surface of the flexible delivery tool, the rolling device including a tubular body defining a channel therein and including a first slit connected to the channel, the first slit and the first channel extending along an entire length of the tubular body, at least one handle hole configured to receive the tie handle positioned on the implantable sheet, and a spout positioned on a distal end portion of the tubular body, the spout configured to attach to a trocar to allow passage of the implantable sheet in a rolled configuration around an outer surface of the delivery tool from the rolling device to the trocar.

9. The surgical kit of paragraph 8, wherein the rolling device further includes a fin and the channel is conical with the channel near distal end portion being narrower than the channel near the proximal end portion.

10. The surgical kit of paragraph 1, further comprising an insertion member including an elongate body extending between a proximal end portion including a handle and a distal end portion including a socket, the socket configured to matingly engage the shaped proximal end of the flexible delivery tool.

11. The surgical kit of paragraph 10, wherein the socket includes a socket protrusion configured to mate with an indentation defined in a thickness of the shaped proximal end portion of the flexible delivery tool.

12. The surgical kit of paragraph 1, wherein the flexible delivery tool is unidirectional.

13. The surgical kit of paragraph 1, wherein the flexible delivery tool is multidirectional and is configured to transition between a unidirectional configuration to a multidirectional configuration, the flexible delivery tool further including at least one pivotable arm which can be pivoted manually or has a natural bias to pivot away from the flexible delivery tool.

14. The surgical kit of paragraph 1, wherein the implantable sheet is a surgical mesh.

15. A package for a kit including at least an implantable sheet and flexible sheet delivery tool, the package comprising:
a base including an area configured to receive an implantable sheet; and
a first channel formed in the base below the area configured to receive the implantable sheet and extending beyond the area configured to receive the implantable sheet, the first channel configured to receive a flexible sheet delivery tool, wherein the first channel widens on a proximal end thereof to form a mouth; and
a recess formed in the base and crossing over the first channel, the recess further including at least one finger engagement recess on each side of the first channel.

16. The package of paragraph 15, wherein the base includes an incline in the area configured to receive the implantable sheet.

17. The package of paragraph 15, wherein the first channel is a gutter configured to prevent direct contact between the implantable sheet and flexible sheet delivery tool prior to use.

18. The package of paragraph 15, further comprising a second channel configured to receive a sheet rolling device configured to wrap the implantable sheet around the flexible sheet delivery tool and a third channel configured to receive an insertion member, the second and third channels formed in a portion of the base beyond the area configured to receive the implantable sheet.

19. The package of paragraph 15, wherein the package is a blister package.

20. The package of paragraph 15, wherein the implantable sheet is a surgical mesh and the flexible sheet delivery tool is a flexible mesh delivery tool.

21. A sheet delivery tool comprising:
a flexible rod including an elongate body extending between a shaped proximal end portion and a distal end portion including a suture aperture defined therethrough and configured to receive a suture, and a sheet attachment clip, the sheet attachment clip positioned proximal to the suture aperture and including a slot defined within the distal end portion and extending longitudinally along a length of the distal end portion.

22. The sheet delivery tool of paragraph 21, wherein the slot is sinusoidal.

23. The sheet delivery tool of paragraph 21, wherein the distal end portion includes at least one crenulation extending outwardly from an outer surface thereof, the crenulation configured to engage openings in an implantable sheet when rolled.

24. The sheet delivery tool of paragraph 21, wherein the slot forms an upper jaw member and a lower jaw member on the distal end portion of the rod, wherein the slot optionally includes at least one tooth or recess.

25. The sheet delivery tool of paragraph 24, wherein the upper jaw member further includes a raised tension arm extending from the upper jaw member at a first angle and above an outer surface of the upper jaw member.

26. The sheet delivery tool of paragraph 24, wherein the upper jaw member further includes a raised compound tension arm extending from the upper jaw member.

27. A method of repairing a ventral hernia comprising:
combining an implantable sheet, a central tie, and a delivery tool to form a sheet-tool assembly,
preparing the sheet-tool assembly for insertion into a patient by using a rolling device and an insertion member to form a rolled sheet-tool assembly,
inserting the rolled sheet-tool assembly into a patient via a trocar using both the rolling device and the insertion member,
deploying the sheet inside the patient,
positioning and fixating the sheet inside the patient, and
withdrawing the delivery tool from the patient.

What is claimed is:

1. A surgical kit for hernia repair comprising:
an implantable sheet having a central tie passing therethrough, the central tie forming a tie loop extending from a bottom side of the implantable sheet and a tie handle positioned on a top side of the implantable sheet, and
a flexible delivery tool including an elongate body extending between a shaped proximal end portion and a distal end portion, the distal end portion including a clip attachment configured to secure a portion of the implantable sheet within the distal end portion of the flexible delivery tool, wherein the elongate body of the flexible delivery tool passes through the tie loop of the central tie.

2. The surgical kit of claim 1, wherein the implantable sheet and the flexible delivery tool are preassembled to be indirectly connected to each other via the central tie, alternatively or additionally wherein at least a portion of an outer edge of the implantable sheet is secured with the clip attachment on the distal end portion of the flexible delivery tool.

3. The surgical kit of claim 1, wherein the clip attachment includes a slot extending longitudinally through the distal end portion of the flexible delivery tool, the slot positioned between an upper jaw member and a lower jaw member.

4. The surgical kit of claim 3, wherein the upper jaw member further includes a raised tension arm extending from the upper jaw member at a first angle and above an outer surface of the upper jaw member.

5. The surgical kit of claim 3, wherein at least one of the upper or lower jaw members includes at least one tooth and at least one of the upper or lower jaw members includes at least one recess configured to receive the at least one tooth.

6. The surgical kit of claim 3, wherein the distal end portion of the flexible delivery tool further comprises a suture aperture defined therethrough and positioned distal to the slot of the attachment clip, the suture aperture configured to receive a looped suture suitable for grasping when withdrawing the flexible delivery tool from a patient.

7. The surgical kit of claim 1, wherein the distal end portion of the flexible delivery tool further comprises at least one crenulation extending outwardly from an outer surface of the distal end portion, the at least one crenulation configured to engage openings in the implantable sheet when rolled.

8. The surgical kit of claim 1, further comprising a rolling device configured to roll the implantable sheet around an outer surface of the flexible delivery tool, the rolling device including a tubular body defining a first channel therein and including a first slit connected to the first channel, the first slit and the first channel extending along an entire length of the tubular body, at least one handle hole configured to receive the tie handle positioned on the implantable sheet, and a spout positioned on a distal end portion of the tubular body, the spout configured to attach to a trocar to allow passage of the implantable sheet in a rolled configuration around the outer surface of the flexible delivery tool from the rolling device to the trocar.

9. The surgical kit of claim 8, wherein the rolling device further includes a fin and the first channel is conical with a diameter of the first channel near the distal end portion of the tubular body being narrower than the diameter of the first channel near a proximal end portion of the tubular body.

10. The surgical kit of claim 1, further comprising an insertion member including an elongate body extending between a proximal end portion of the insertion member including a handle and a distal end portion of the insertion member including a socket, the socket configured to matingly engage the shaped proximal end portion of the flexible delivery tool, optionally wherein the socket includes a socket protrusion configured to mate with an indentation defined in a thickness of the shaped proximal end portion of the flexible delivery tool.

11. The surgical kit of claim 1, wherein the flexible delivery tool is unidirectional or alternatively wherein the flexible delivery tool is multidirectional and is configured to transition between a unidirectional configuration to a multidirectional configuration, the flexible delivery tool further including at least one pivotable arm which can be pivoted manually or has a natural bias to pivot away from the flexible delivery tool.

12. A package for a surgical kit comprising:
a base including an area configured to receive an implantable sheet; and
a first channel formed in the base below the area configured to receive the implantable sheet and extending beyond the area configured to receive the implantable sheet, the first channel configured to receive a flexible sheet delivery tool such that the implantable sheet is stored above the flexible sheet delivery tool, wherein the first channel widens on a proximal end thereof to form a mouth; and
a recess formed in the base and crossing over the first channel, the recess further including at least one finger engagement recess offset from the first channel.

13. The package of claim 12, wherein:
the base includes an incline in the area configured to receive the implantable sheet;
the first channel is a gutter configured to prevent direct contact between the implantable sheet and flexible sheet delivery tool prior to use; or
the package further comprises a second channel configured to receive a sheet rolling device configured to wrap the implantable sheet around the flexible sheet delivery tool and a third channel configured to receive an insertion member, the second and third channels formed in a portion of the base beyond the area configured to receive the implantable sheet.

14. A sheet delivery tool comprising:
a flexible rod including an elongate body extending between a shaped proximal end portion and a distal end portion including a suture aperture defined therethrough and configured to receive a suture, and a sheet attachment clip, the sheet attachment clip positioned proximal to the suture aperture and including a slot defined within the distal end portion and extending longitudinally along a length of the distal end portion, wherein the slot is sinusoidal or the distal end portion includes at least one crenulation extending outwardly from an outer surface thereof, the at least one crenulation configured to engage openings in an implantable sheet when rolled.

15. The sheet delivery tool of claim 14, wherein the slot forms an upper jaw member and a lower jaw member on the distal end portion of the rod.

16. The sheet delivery tool of claim 15, wherein the upper jaw member further includes a raised compound tension arm extending from the upper jaw member.

17. The sheet delivery tool of claim 15, wherein:
the slot includes at least one tooth;
the slot includes at least one recess; or
the upper jaw member further includes a raised tension arm extending from the upper jaw member at a first angle and above an outer surface of the upper jaw member.

* * * * *